(12) United States Patent
Richards et al.

(10) Patent No.: US 11,935,008 B2
(45) Date of Patent: Mar. 19, 2024

(54) DETERMINING COHESION OF HEALTHCARE GROUPS AND CLINICS BASED ON BILLED CLAIMS

(71) Applicant: Milliman Solutions LLC, Seattle, WA (US)

(72) Inventors: Robert Richards, Salt Lake City, UT (US); David Muhlestein, Salt Lake City, UT (US)

(73) Assignee: Milliman Solutions LLC

( * ) Notice: Subject to any disclaimer, the term of this patent is extended or adjusted under 35 U.S.C. 154(b) by 700 days.

(21) Appl. No.: 16/932,575

(22) Filed: Jul. 17, 2020

(65) Prior Publication Data

US 2021/0158911 A1    May 27, 2021

Related U.S. Application Data

(60) Provisional application No. 62/939,349, filed on Nov. 22, 2019.

(51) Int. Cl.
  *G16H 40/20* (2018.01)
  *G06F 16/24* (2019.01)
  *G06F 16/28* (2019.01)
  *G06F 16/90* (2019.01)
  *G06F 21/60* (2013.01)
  (Continued)

(52) U.S. Cl.
  CPC ........... *G06Q 10/105* (2013.01); *G06F 16/24* (2019.01); *G06F 16/284* (2019.01); *G06F 16/288* (2019.01); *G06F 16/90* (2019.01); *G06F 21/602* (2013.01); *G06F 21/6245* (2013.01); *G06Q 10/06398* (2013.01); *G06Q 10/10* (2013.01); *G06Q 30/0185* (2013.01); *G06Q 30/04* (2013.01); *G06Q 40/12* (2013.12); *G06Q 50/265* (2013.01); *G16H 10/60* (2018.01); *G16H 40/00* (2018.01); *G16H 40/20* (2018.01);
  (Continued)

(58) Field of Classification Search
  CPC ...... G16H 40/00; G16H 40/20; G06Q 10/105; G06Q 10/06398
  See application file for complete search history.

(56) References Cited

U.S. PATENT DOCUMENTS

| | | |
|---|---|---|
| 8,214,232 B2 | 7/2012 | Tyler et al. |
| 8,566,117 B1 | 10/2013 | Troutt et al. |

(Continued)

OTHER PUBLICATIONS

Cohen, Genna R., et al. "Leveraging diverse data sources to identify and describe US health care delivery systems." eGEMs 5.3 (2017). (Year: 2017).*

(Continued)

*Primary Examiner* — Mamon Obeid
*Assistant Examiner* — Chance L Smith
(74) *Attorney, Agent, or Firm* — TechLaw Ventures, PLLC; Terrence J. Edwards

(57) ABSTRACT

Determining cohesion of healthcare groups and clinics based on billed claims. A method includes determining a target office billing identifier associated with one or more of a healthcare group or a healthcare clinic and determining a practitioner billing a carrier claim comprising the target office billing identifier. The method includes identifying a plurality of carrier claims billed by the practitioner over a time period. The method includes calculating a proportion of the plurality of carrier claims that comprise the target office billing identifier.

30 Claims, 15 Drawing Sheets

(51) Int. Cl.
*G06F 21/62* (2013.01)
*G06Q 10/0639* (2023.01)
*G06Q 10/10* (2023.01)
*G06Q 10/105* (2023.01)
*G06Q 30/018* (2023.01)
*G06Q 30/04* (2012.01)
*G06Q 40/12* (2023.01)
*G06Q 50/26* (2012.01)
*G16H 10/60* (2018.01)
*G16H 40/00* (2018.01)
*G16H 50/70* (2018.01)
*G16H 70/20* (2018.01)
*G06Q 40/08* (2012.01)

(52) U.S. Cl.
CPC ............ *G16H 50/70* (2018.01); *G16H 70/20* (2018.01); *G06Q 40/08* (2013.01)

(56) References Cited

U.S. PATENT DOCUMENTS

| | | | |
|---|---|---|---|
| 8,688,607 B2* | 4/2014 | Pacha | G06Q 40/08 706/45 |
| 10,535,430 B1 | 1/2020 | Fischer et al. | |
| 10,628,834 B1 | 4/2020 | Agarwal et al. | |
| 10,991,457 B1 | 4/2021 | Hallemeier et al. | |
| 2003/0083903 A1 | 5/2003 | Myers | |
| 2004/0078228 A1* | 4/2004 | Fitzgerald | G06Q 10/10 705/2 |
| 2005/0091080 A1 | 4/2005 | Biats, Jr. | |
| 2007/0067247 A1* | 3/2007 | Brookhart | G06Q 30/0283 705/400 |
| 2010/0114607 A1 | 5/2010 | Kress et al. | |
| 2010/0228564 A1 | 9/2010 | Kharraz Tavakol et al. | |
| 2011/0125531 A1 | 5/2011 | Seare et al. | |
| 2013/0073313 A1 | 3/2013 | Christakis et al. | |
| 2013/0110533 A1 | 5/2013 | Paul et al. | |
| 2014/0164020 A1* | 6/2014 | Thesman | G06F 3/04842 705/3 |
| 2014/0278479 A1 | 9/2014 | Wang et al. | |
| 2014/0372148 A1* | 12/2014 | Reddy | G06Q 50/22 705/3 |
| 2015/0046181 A1 | 2/2015 | Adjaoute | |
| 2015/0278462 A1 | 10/2015 | Smoley et al. | |
| 2016/0019357 A1 | 1/2016 | Marzula et al. | |
| 2016/0132646 A1* | 5/2016 | Jones | G16H 70/00 705/2 |
| 2016/0188819 A1 | 6/2016 | Subramanian et al. | |
| 2017/0017760 A1 | 1/2017 | Freese et al. | |
| 2017/0293723 A1* | 10/2017 | Friesen | G06Q 10/10 |
| 2018/0240195 A1 | 8/2018 | Bogle et al. | |
| 2019/0385126 A1 | 12/2019 | Morrow et al. | |
| 2020/0043579 A1 | 2/2020 | McEwing | |
| 2020/0272740 A1 | 8/2020 | Obee et al. | |
| 2020/0411181 A1 | 12/2020 | Agnello et al. | |
| 2021/0133605 A1 | 5/2021 | Greene et al. | |
| 2021/0141834 A1 | 5/2021 | Mac Manus et al. | |
| 2021/0158295 A1 | 5/2021 | Muhlestein et al. | |
| 2021/0158452 A1 | 5/2021 | Muhlestein et al. | |
| 2021/0158912 A1 | 5/2021 | Richards et al. | |
| 2021/0158913 A1 | 5/2021 | Richards et al. | |
| 2021/0158942 A1 | 5/2021 | Richards et al. | |
| 2021/0158943 A1 | 5/2021 | Richards et al. | |
| 2021/0158944 A1 | 5/2021 | Richards et al. | |
| 2021/0158945 A1 | 5/2021 | Richards et al. | |

OTHER PUBLICATIONS

Madison et al., "Hospital-physician affiliation and patient treatments, expenditures, and outcomes," Health Service Research, 39(2), 257(22), Apr. 2004, 14 pages (Year: 2004).

Barnett et al., "Mapping Physician Networks with Self-Reported and Administrative Data," HSR: Health Service Research, 46:5 (Oct. 2011), pp. 1592-1609 (Year: 2011).

Bynum et al., "Assigning Ambulatory Patients and Their Physicians to Hospitals: A Method for Obtaining Population-Based Provider Performance Measurements," HSR: Health Services Research, 42:1, Part 1 (Feb. 2007), pp. 45-60 (Year: 2007).

* cited by examiner

DETERMINING COHESION OF HEALTHCARE GROUPS AND CLINICS BASED ON BILLED CLAIMS

CROSS-REFERENCE TO RELATED APPLICATION

This application claims the benefit of U.S. Provisional Patent Application No. 62/939,349, filed Nov. 22, 2019, titled "IDENTIFICATION OF EMPLOYMENT RELATIONSHIPS BETWEEN HEALTHCARE PRACTITIONERS AND HEALTHCARE FACILITIES," which is incorporated herein by reference in its entirety, including but not limited to those portions that specifically appear hereinafter, the incorporation by reference being made with the following exception: In the event that any portion of the above-referenced provisional application is inconsistent with this application, this application supersedes the above-referenced provisional application.

TECHNICAL FIELD

The disclosure relates generally to the analysis of healthcare systems and particularly to calculating cohesion and capture metrics between healthcare entities.

BACKGROUND

The healthcare industry is extraordinarily complex. Specifically, in the United States, relationships between healthcare practitioners, clinics, facilities, groups, and systems are complex and interwoven such that it can be challenging to identify relationships between different entities. One practitioner may see patients that are part of different systems, health insurance networks, or groups. Further, the practitioner may be associated with more than one facility or clinic. The interwoven relationships between healthcare entities makes it challenging to determine if a certain practitioner is associated with or employed by a certain facility, clinic, group, or system. Additionally, other relationships between practitioners, facilities, clinics, groups, and systems throughout the healthcare industry are difficult to identify and quantify.

In some instances, it is necessary or beneficial to understand the relationships between healthcare entities. For example, a health insurance provider seeking to create an in-network selection of providers may need to know which practitioners are associated with which facilities, clinics, groups, or systems. Further for example, a manufacturer or seller of medical devices or pharmaceuticals may benefit from understanding the business relationships between practitioners, facilities, clinics, groups, and systems. In some instances, for example, the manufacturer or seller may sell a medical device or pharmaceutical to a single group, and this would in turn lead to distribution of that medical device or pharmaceutical to hundreds of practitioners associated with the group. These relationships between healthcare entities are nearly impossible to identify or quantify.

In light of the foregoing, disclosed herein are systems, methods, and devices for identifying relationships between healthcare entities.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where.

DETAILED DESCRIPTION

Figure 1:
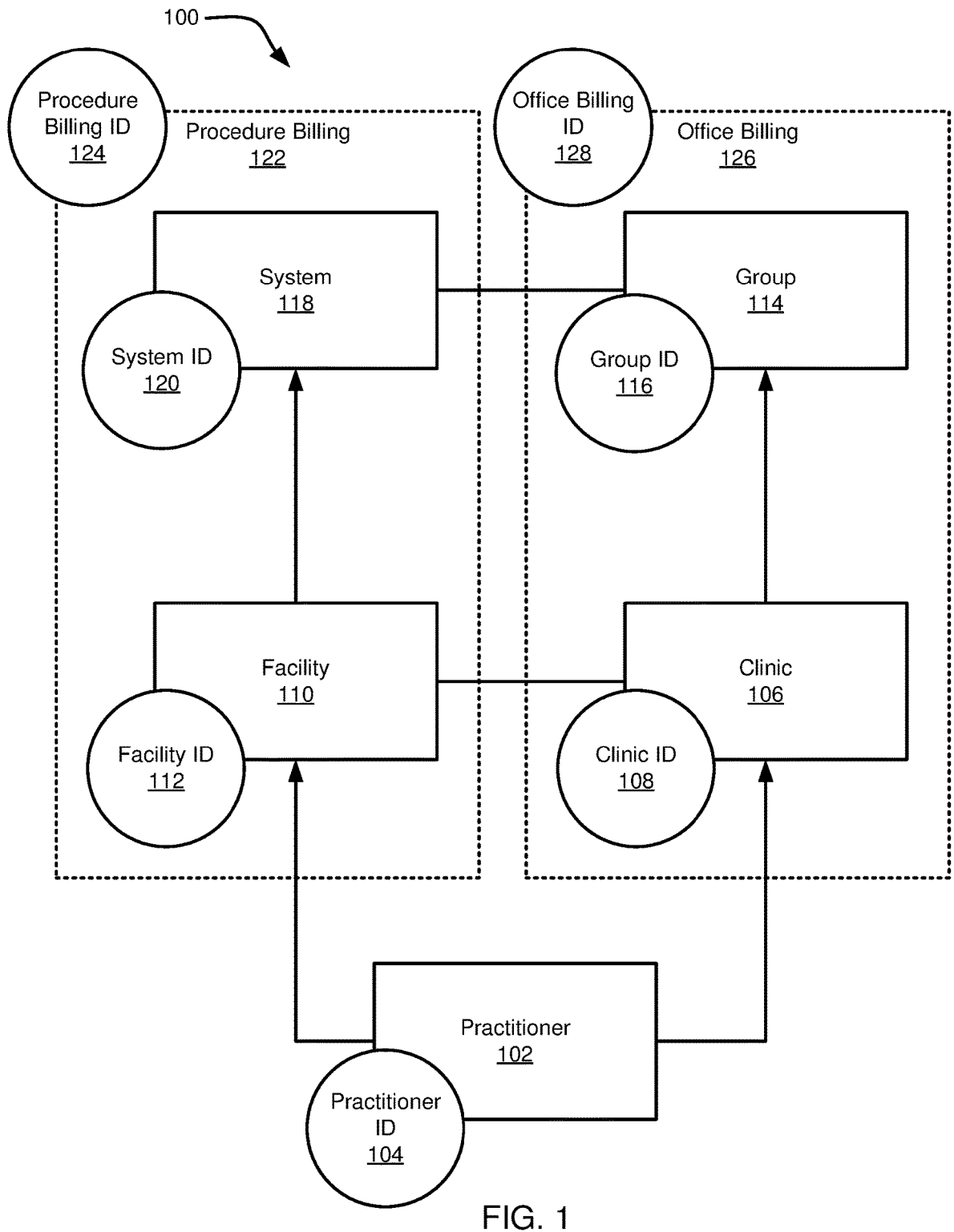
FIG. 1 is a schematic diagram of a framework outlining affiliations between healthcare entities.

Disclosed herein are systems, methods, and devices for calculating cohesion metrics between healthcare entities. Specifically, disclosed herein are means for measuring the cohesion of practitioners that practice at healthcare clinics and groups and further for measuring the cohesion of practitioners performing procedures at healthcare facilities and systems. Additionally, disclosed herein are means for quantifying the cohesion of practitioners who have been captured by or are employed by a healthcare facility or system. Additionally, disclosed herein are means for linking healthcare procedure billing entities with office billing entities based on billed claims.

Current understanding of the healthcare industry in the United States is extremely fragmented. In some instances, it is difficult or impossible to identify systems of care including financial, employment, and enrollment relationships between healthcare entities. The healthcare industry uses multiple data sources for storing billing, procedure, and facility records. There is no one data source that is ideal or reliable for identifying the numerous relationships between healthcare entities. Because healthcare data is fragmented, it can be beneficial to match different types of healthcare data. The matched data can be assessed to identify and quantify relationships between different entities.

Embodiments of the disclosure leverage multiple data sources to describe relationships precisely and completely between healthcare entities. Relationships between practitioners and other healthcare entities cannot be viewed as binary. There are multiple types of affiliations between healthcare entities, and each affiliation may be characterized in terms of its strength. An affiliation reported as merely binary (i.e. yes/no, exists/does not exist, and so forth) masks important information.

Embodiments of the disclosure begin at the level of individual practitioner billing and procedure codes and build from there to identify and quantify relationships between other healthcare entities. By tracking the relationships of individual practitioners to higher level entities, the connections between practitioners and multiple other entities can be identified. This is an improved and more streamlined method when compared with viewing all organizations as discrete, mutually exclusive sets of practitioners.

Embodiments of the disclosure interpret affiliation metrics based on an individualized perspective. For example, a physician's affiliation with a hospital has two perspectives: the physician's perspective and the hospital's perspective. The physician may view the hospital as a necessary portion of the practice that enables the physician to perform certain procedures. The hospital may view the physician as one of many, and the physician's procedures performed at the hospital may represent a very small portion of all procedures performed at the hospital. Understanding affiliations from both perspectives is more informative than viewing the affiliations from only one perspective.

Embodiments of the disclosure describe affiliations in terms of real-world activities that link practitioners to other healthcare entities. This can be performed by assessing disparate data sources in terms of real-world actions or relationships. Some actions, such as referrals or billing of carrier claims 402, may come naturally from a single data source. Other actions, such as geographic practice locations and clinic ownership, require synthesis of multiple data sources. The goal is not merely to represent the data sources, but to leverage the data sources to represent the real world. This results in new metrics and relationships that did not exist before. In embodiments of the disclosure, raw data is manipulated to identify real-world relationships that could not previously be identified or quantified.

Embodiments of the disclosure state affiliations between healthcare entities through action. For example, rather than querying practitioners and other healthcare entities about how they believe they are affiliated, it is more accurate to assess actual behaviors that illuminate real-world relationships free from spin, bias, ignorance, misunderstanding, or self-reported outcomes.

Before the structures, systems, and methods for merging healthcare data are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Referring now to the figures, FIG. 1 illustrates a framework 100 that outlines affiliations between healthcare entities. The framework 100 is built from the ground up and begins with the practitioner 102. The practitioner may be affiliated with facilities 110 and/or clinics 106. A facility 110 may be affiliated with a system 118. A clinic 106 may be affiliated with a group 114. There may be affiliations between systems 118 and groups 114 and between facilities 110 and clinics 106. The claims billed in association with facilities 110 and systems 118 may be referred to herein as procedure billing 122. The procedure billing 122 claims may be filed as facility claims (see 404 at FIG. 4). The claims billed in associated with clinics 106 and groups 114 may be referred to herein as office billing 126. The office billing 126 claims may be filed as carrier claims (see 402 at FIG. 4).

In an embodiment of the framework 100, a distinction is drawn between systems 118 that may own facilities 110, and groups 114 that may own clinics 106. This distinction is made for illustrative purposes and to increase the accuracy of conclusions drawn from assessing healthcare affiliations.

In some instances, this distinction does not exist in the real world, and systems 118 and groups 114 are the same entity. This approach permits individual practitioner behaviors to be leveraged to describe the relationships of higher-level entities with one another.

The practitioner 102 is a healthcare practitioner such as a physician (Doctor of Medicine), physician assistant, nurse practitioner, podiatrist, dentist, chiropractor, psychologist, optometrist, nurse midwife, clinical social worker, and so forth. The practitioner 102 may be a single person licensed to provide healthcare advice or guidance, perform procedures, prescribe medications, and so forth. The practitioner 102 may be a solo practitioner, may be associated with a group of other practitioners 102 in a clinic 106 or other group setting, may be employed by a facility 110 such as a hospital, may be employed as an in-house practitioner, and so forth. In some instances, it can be beneficial to identify and quantify the practitioner's 102 relationships with other entities such as clinic 106, facilities 440-110, groups 114, and systems 118.

The practitioner 102 may be associated with a practitioner ID 104. In some embodiments, the practitioner ID is an individual NPI (National Provider Identifier). In the United States, an individual National Provider Identifier (NPI) is a Health Insurance Portability and Accountability Act (HIPAA) administrative standard. An individual NPI is a unique identification number for covered healthcare providers. In the United States, covered healthcare providers, health plans, and healthcare clearinghouses are directed to use NPIs in administrative and financial transactions. It should be appreciated that the practitioner 102 may be associated with any unique identifier and does not need to be associated with a National Provider Identifier. The use of some other unique identifier does not depart from the scope of the disclosure. The practitioner ID 104 is a unique code associated with the practitioner 102. It should be appreciated that the practitioner ID 104 is any unique code associated with the practitioner 102 and can include other codes without departing from the scope of the disclosure.

The clinic 106 is a group of practitioners, a single practitioner, or some other entity that is primarily focused on the care of outpatients. The clinic 106 may be an outpatient clinic, an ambulatory care clinic, a physical therapy clinic, a specialist clinic, an urgent care clinic, an employer-funded in-house healthcare clinic, and so forth. The clinic 106 may be a group of practitioners that practice together at the same physical location or at different physical locations. The clinic 106 may include one or more practitioners 102 that practice telehealth care over the phone, over video communications, or by some other form of communication. The clinic 106 may be privately operated or publicly managed and funded. The clinic 106 may be suited for covering primary healthcare needs or specialized outpatient healthcare needs for populations of communities, in contrast with larger hospitals that offer specialized treatments and admit inpatients for overnight stays. The clinic 106 is not limited to only providing outpatient care.

The clinic 106 may be associated with a clinic ID 108. In some embodiments, the clinic ID 108 is an organization NPI (National Provider Identifier). In the United States, an organization National Provider Identifier (NPI) is a Health Insurance Portability and Accountability Act (HIPAA) administrative standard. An organization NPI is a unique identification number for covered healthcare clinics. The clinic ID 108 is a unique code associated with the clinic 106. If the clinic 106 has multiple geographic locations, then each of the multiple geographic locations for the clinic 106 may have a unique clinic ID 108. In some instances, two or more locations for the same clinic 106 share a clinic ID 108. It should be appreciated that the clinic 106 may be associated with any unique identifier and does not need to be associated with an organization NPI. The use of some other unique identifier does not depart from the scope of the disclosure.

The facility 110 is a physical or virtual healthcare location where an individual can receive care from a practitioner 102. The facility 110 may include hospitals, ambulatory surgical centers, birth centers, blood banks, dialysis centers, hospice centers, imaging and radiology centers, mental health and addiction treatment centers, nursing homes, orthopedic and other rehabilitation centers, telehealth systems, and so forth. In some implementations, it is not necessary to provide a formal definition for a facility 110 versus a clinic 106, and this distinction can be drawn based on the factual circumstances of various healthcare entities.

In an example embodiment, the facility 110 is linked to a facility ID 112. In some embodiments, the facility ID 112 is a Centers for Medicare and Medicaid Services (CMS) Certification Number, which is referred to as a CCN. In the United States, the CCN is the facility's 110 unique identification code that is linked to the facility's 110 provider agreement for Medicare billing. In some instances, the CCN is referred to as the facility's 110 "provider number." The facility ID 112 is used for submitting and reviewing the facility's 110 cost reports. It should be appreciated that the facility 110 may be associated with any unique identifier and does not need to be associated with a CCN. The use of some other unique identifier does not depart from the scope of this disclosure.

The group 114 is a healthcare entity that owns one or more clinics 106. The group 114 may alternatively be referred to as a "provider group." In some instances, there is no real-world distinction between groups 114 and systems 118, and this distinction is made in the systems, methods, and devices disclosed herein for the purpose of improving analytics on various healthcare entities. In some instances, a single healthcare entity may be referred to as a group 114 and as a system 118 for purposes of improving the analytics described herein.

The group 114 may be associated with a group ID 116. In some embodiments, the group ID 116 is a PAC ID (Practice Access Code ID) assigned by PECOS (Provider Enrollment, Chain and Ownership System). The PECOS is a system used in the United States and enables practitioners and other healthcare facilities to register with the Centers for Medicare and Medicare Services. PECOS is the Provider, Enrollment, Chain, and Ownership System. The system 118 may further be associated with the group ID 116. In some cases, a group 114 and a system 118 are the same entity and are associated with the same group ID 116. In some cases, a group 114 and a system 118 are separate entities to the degree that the group 114 is associated with its own group ID 116 and the system 118 is associated with its own system ID 120.

The system 118 is a healthcare entity that owns one or more facilities 110. In some instances, there is no real-world distinction between groups 114 and systems 118, and this distinction is made in the systems, methods, and devices disclosed herein for the purpose of improving analytics on various healthcare entities. In some instances, a single healthcare entity may be referred to as a group 114 and as a system 118 for purposes of improving the analytics described herein.

There are numerous metrics that can be calculated based on the relationships between practitioners 102, clinics 106, facilities 110, groups 114, and systems 118. In some cases, the metrics are determined based on claims billed by any of the entities described in FIG. 1. Some basic affiliation metrics that can be calculated include practitioner billing metrics, clinic billing metrics, practitioner enrollment metrics, clinic enrollment metrics, practitioner-group billing metrics, group billing metrics, practitioner-facility procedure volume metrics, facility procedure volume metrics, practitioner-facility employment metrics, facility-clinic distance metrics, and others. The practitioner billing metric is the proportion of a practitioner's total carrier claims 402 billed to a certain clinic associated with a specific clinic ID 108. The clinic billing metric is the proportion of total carrier claims 402 billed under a clinic performed by a given practitioner. The practitioner enrollment metric is the clinics at which a practitioner is enrolled in the PECOS. The clinic enrollment is the practitioner(s) enrolled in the PECOS under a clinic. The practitioner-group billing is the proportion of the practitioner's carrier claims 402 billed under any of the group's clinics. The group billing is the proportion of all carrier claims 402 billed under any of the group's clinics that were performed by a specific practitioner. The practitioner-facility procedure volume is the proportion of a practitioner's total procedure claims performed at each facility. The facility-procedure volume is the proportion of the procedures performed at the facility performed by each practitioner. The practitioner-facility employment is the level of confidence that the practitioner is employed by a given facility. The facility or clinic distance is the distance between a clinic and a facility in miles or some other distance measurement.

Practitioners 102 bill for services and devices through procedure billing 122 and office billing 126. In most implementations, when a practitioner 102 performs a procedure at a hospital, surgical center, or other facility 110, the practitioner's 102 activity leads to a facility claim 404 that identifies the appropriate facility 110. Further in most implementations, when a practitioner 102 performs an office visit or other service at a clinic 106, the practitioner 102 bills a carrier claim 402 that identifies the appropriate clinic 106. The procedure billing 122 submitted by one or more practitioners 102 can be assessed to identify and quantify relationships between facilities 110 and systems 118. Similarly, the office billing 126 submitted by one or more practitioners 102 can be assessed to identify and quantify relationships between clinics 106 and groups 114.

As discussed herein, procedure billing 122 may be associated with a procedure billing identifier 124. The procedure billing identifier 124 may comprise one or more of the system identifier 120 or the facility identifier 112. Therefore, the procedure billing identifier 124 includes any applicable identifier associated with procedure billing 122. The procedure billing identifier 124 is a means for identifying one or more of a system 118 or a facility 110. The procedure billing identifier 124 may be included in a procedure billing 122, such as a facility claim 404 or another claim associated with a system 118 and/or facility 110. The procedure billing identifier 124 as discussed herein includes a system identifier 120 and/or a facility identifier 112 as applicable in the pertinent use-case.

Further as discussed herein, a "procedure practitioner" refers to a practitioner billing claims for procedures performed under a procedure billing identifier 124. This includes practitioners associated with claims comprising one or more of a facility identifier 112 or a system identifier 120. The term procedure practitioner as used herein does not necessarily refer to a practitioner that performs procedures or bills patients for procedure work. A procedure practitioner may include any practitioner associated with one or more claims comprising a procedure billing identifier 124.

As discussed herein, office billing 126 may be associated with an office billing identifier 128. The office billing identifier 128 may comprise one or more of the group identifier 116 or the clinic identifier 108. Therefore, the office billing identifier 128 includes any applicable identifier associated with office billing 126. The office billing identifier 128 is a means for identifying one or more of a group 114 or a clinic 106. The office billing identifier 128 may be included in an office billing 126 such as a carrier claim 402 or another claim associated with a group 114 and/or a clinic 106. The office billing identifier 128 as discussed herein includes a group identifier 116 and/or a clinic identifier 108 as applicable in the pertinent use-case.

Further as discussed herein, an "office practitioner" refers to a practitioner billing claims under an office billing identifier 128. This includes practitioners associated with claims comprising one or more of a clinic identifier 108 or a group identifier 116. The term office practitioner as used herein does not necessarily refer to a practitioner that performs office work or bill patients for procedures performed at an office or billed under a carrier claim. An office practitioner may include any practitioner associated with one or more claims comprising an office billing identifier 128.

Figure 2:
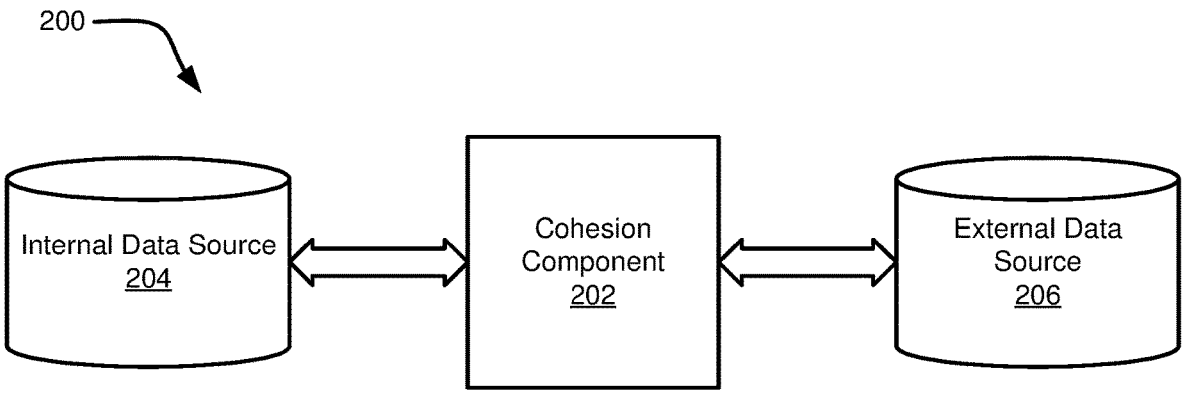
FIG. 2 is a schematic diagram of a system for data communication between a cohesion component and internal and external data sources.

FIG. 2 is a schematic diagram of a system 200 for data communication between a cohesion component 202 and internal and external data sources. The cohesion component 202 identifies and manipulates data from multiple sources to determine cohesion between various healthcare entities. The matched data can then be analyzed to identify and quantify relationships between different healthcare entities. The cohesion component 202 performs these calculations based on real-world claim data and/or enrollment data that can be stored in a combination of internal and external data sources. The cohesion component 202 may communicate with one or more of an internal data source 204 and an external data source 206. The internal data source 204 may be a database, data store, or other memory device that is "internal" to the cohesion component 202 or is managed by the same entity as the cohesion component 202. The external data source 206 may be a database, data store, or other memory device that is "external" to the cohesion component 202 or is managed by some other entity such that the cohesion component 202 must access that data by way of an Application Program Interface (API), by receiving a file, by accessing an external server, and so forth.

In an embodiment, the cohesion component 202 communicates directly with an external data source 206 that is managed or owned by a third-party entity. In an embodiment, the external data source 206 is owned and managed by the Medicare system operated by the United States government, or by some other entity that has been tasked with managing data for the Medicare system. In an embodiment, the external data source 206 is a relational database, and the cohesion component 202 communicates with the relational database by way of an Application Program Interface (API). In an embodiment, the external data source 206 is an encrypted hard drive that has been shared with the cohesion component 202. In an embodiment, the external data source 206 is a virtual data center, and the cohesion component 202 accesses the data on a virtual server after signing in or undergoing some other authentication step.

In an embodiment, the cohesion component 202 communicates with an internal data source 204 that is not managed by some other third-party entity. The internal data source 204 may include a file that has been downloaded or otherwise received from some third-party entity, such as the Medicare system. After the file has been downloaded, the file can be managed and manipulated by the cohesion component 202. The internal data source 204 may include an encrypted hard-drive or downloaded encrypted file that is provided by a third-party, such as the Medicare system.

The cohesion component 202 may receive and translate information from multiple different sources. In an example implementation, the cohesion component 202 receives enrollment information from a central data warehouse that may be operated internally or by a third-party. The cohesion component 202 further receives claims data from a different source, for example via a secure connection to a virtual data store by way of an API, by accessing an encrypted hard drive, or accessing an encrypted file that has been downloaded by way of a network connection.

In an embodiment, the data stored in the internal data source 204 has been "cleaned" or pared down to only include necessary or critical information. This can be beneficial to ensure the totality of the data is a usable size that can be efficiently queried, analyzed, and manipulated. For example, the raw data retrieved from the external data source 206 may include numerous data fields that are not necessary for identifying a certain relationship between healthcare entities. The unnecessary data may be eliminated, and only the necessary data may be stored on the internal data source 204. In an embodiment, the raw data is cleaned and stored in a relational database.

In an embodiment, the cohesion component 202 analyzes information stored in the internal data source 204 and/or the external data source 206 by identifying relationships between individual practitioners 102 and their associated clinics 106 and groups 114. In an example use-case, the cohesion component 202 identifies that Doctor A is performing work for Clinic B. The cohesion component 202 then identifies all the practitioners that associate with Clinic B and assesses the carrier claims billed by those practitioners. The cohesion component 202 aggregates the claim information for all practitioners in Clinic B and combines the information in an effort to answer specific questions, such as whether and to what extent practitioners 102 billing at the clinic 108 are also billing at other clinics 108.

The cohesion component 202, or some other module or component in communication with the cohesion component 202, may create intermediary files or tables within a relational database. The intermediary files or tables may include certain information columns that are pertinent to answer a specific question, such as identifying or quantifying a relationship between two or more healthcare entities. This can be beneficial to ensure that each intermediary file or table is no bigger than it needs to be to include all necessary information for answering the specific question. This decreases the amount of disc storage and/or Random-Access Memory (RAM) needed to analyze the information and calculate the answer to the specific question.

Figure 3:
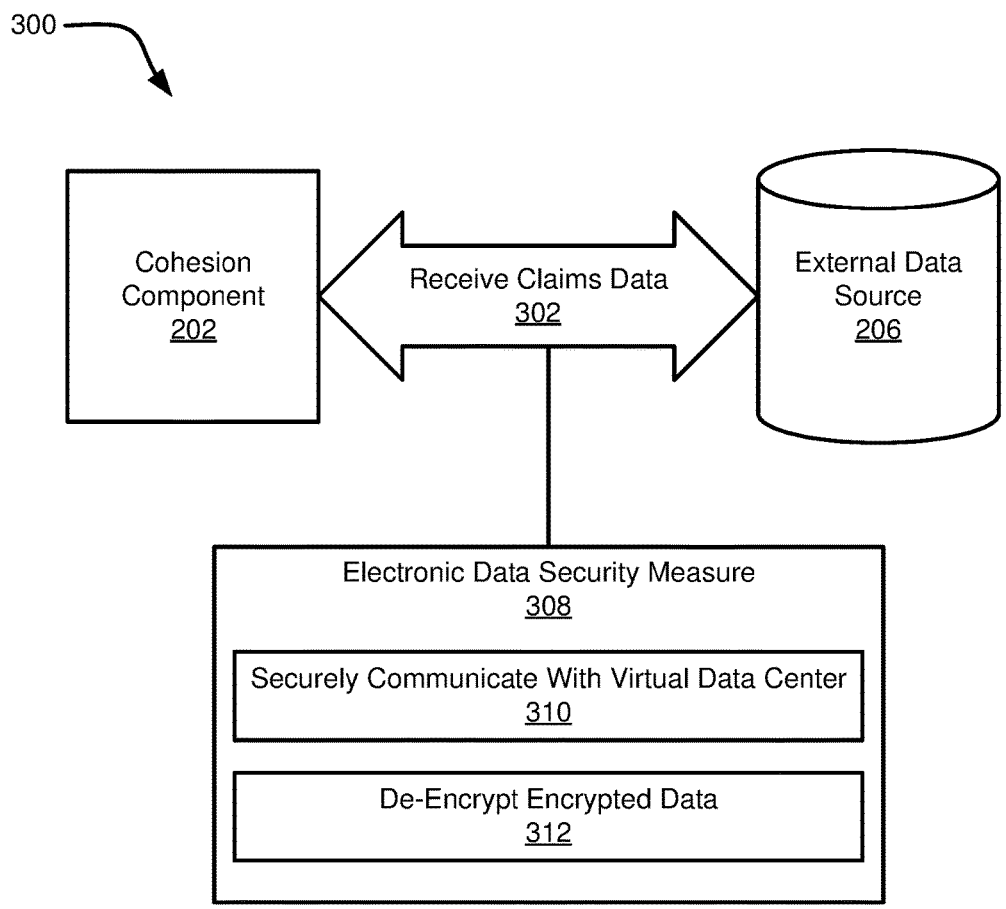
FIG. 3 is a schematic diagram of a system for performing electronic data security measures on data received from an external data source.

FIG. 3 is a schematic diagram of a system 300 for performing electronic data security measures on data received from the external data source 206. The cohesion component 202 receives claims data (see 302) from an external data source 206. The claims data may include carrier claims, facility claims, and other claims generated or processed by private or public healthcare entities. Claims data includes sensitive information such protected personal information (PPI) and personal identifiable information (PII), and therefore, the claims data must be encrypted or otherwise secured.

In an embodiment, the cohesion component 202 receives claims data by securely communicating with a virtual data center (see 310). The virtual data center may be provided by a private or public healthcare entity. In an embodiment, an account is created for a user associated with the cohesion component 202, and the user can sign into the virtual data center with the account. The user can then access the data stored in the virtual data center 310 by way of the account. The data may be encrypted or non-encrypted based on the security measures of the virtual data center. In an embodiment, the data is non-encrypted when viewed by way of a network connection, and the data is encrypted if downloaded for offline use and manipulation. If the data is downloaded in an encrypted form, then the data must be de-encrypted prior to analysis and manipulation.

In an embodiment, the cohesion component 202 receives claims data by way of an encrypted hard drive. The encrypted hard drive may be provided by the source of the data, such as private or public healthcare entity. In an embodiment, the cohesion component 202 receives claims data by way of an encrypted file that has been downloaded by way of a network connection. The cohesion component 202 undergoes an electronic data security measure 308 by de-encrypting the claims data (see 312).

Figure 4:
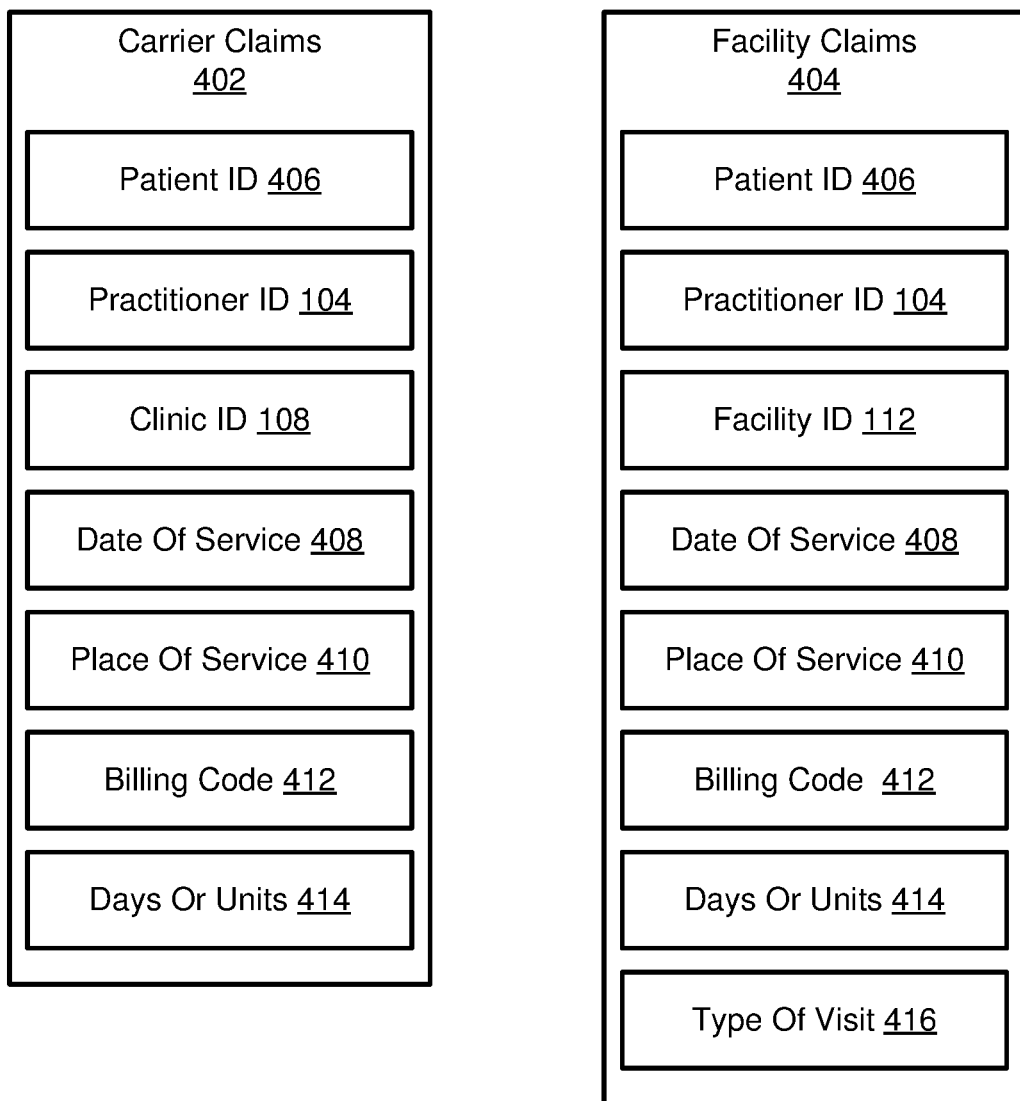
FIG. 4 is a schematic diagram illustrating exemplary data points included in a carrier claim and a facility claim.

FIG. 4 is a schematic diagram illustrating exemplary components of carrier claims 402 and facility claims 404. A carrier claim 402 is a non-institutional medical billing claim submitted by or on behalf of a practitioner 102. The carrier claim 402 may be billed for outpatient or inpatient services. The carrier claims 402 used by the data merging component 202 may include carrier claims 402 submitted through the Medicare system implemented in the United States and may additionally include carrier claims for private entities such as private health insurance agencies. If the carrier claims 402 include Medicare claims, then the carrier claim may be submitted on the health insurance claim form CMS-1500 used by the United States Medicare system.

Carrier claims 402 include information about a service provided by a practitioner 102 in an outpatient or inpatient setting. In some instances, only a portion of the information included in the carrier claim 402 is relevant to the analysis of whether a relationship exists between two or more healthcare entities. Carrier claims 402 may include a patient identifier (ID) 406, which may include a numerical or alphanumerical code assigned to the patient, and may further include the patient's name, address, or other contact information. Carrier claims 402 further include a practitioner ID 104 which may specifically include an individual NPI. The carrier claim 402 may include a clinic ID 108, or some other information identifying the name, location, or contact information of the clinic under which the service was performed. The carrier claim 402 includes an indication of the date of service 408 when the service was performed or on what date the service began if the service extended over multiple days. The carrier claim 402 includes an indication of the place of service 410, and this may be a numerical or alphanumerical code identifying a type of facility, and may also include a name, address, or other contact information for the facility. The carrier claim 402 includes one or more billing codes 412 identifying the services or procedures that were performed by the practitioner 102. The billing code 412 may include a Healthcare Common Procedure Coding System (HCPCS) code. The carrier claim 402 may further include an indication of the days or units 414 indicating a duration of time the procedure occurred.

The facility claims 404 may include similar information. If the facility claims 404 include Medicare claims, then the facility claims may be submitted on the health insurance claim form UB-40 used by the United States Medicare system. The facility claims 404 may include, for example, the patient ID 406, practitioner ID 104, facility ID 112, date of service 408, place of service 410, billing code 412, days or units 414, and an indication of the type of visit 416. The facility ID 112 identifies the facility at which the procedure was performed, and may take the form of an NPI, CMS Certification Number or CCN, or some other way of identifying the name, location, and contact information of the facility. The indication of the type of visit 416 may be a numerical code indicating whether the visit was an emergency, an outpatient visit, an inpatient visit, and so forth.

Carrier claims 402 may include additional information not illustrated in FIG. 4, For example, carrier claims 402 may include an indication of whether the bill is being submitted through a government-funded plan such as Medicare, Medicaid, Tricare, or CHAMPVA, or a private health insurance plan. The carrier claim 402 may include insurance information, such as the insured's ID number, name, address, birth date, policy name, group number, policy number, whether there is an additional health benefit plan, and so forth. The patient ID 406 information may include the patient's name, address, telephone number, and so forth. The carrier claim 402 may include an indication of whether the patient's condition is related to employment, an automobile accident, or some other accident. The date of service 408 information may include an indication of what date the current illness, injury, pregnancy, or other condition began. The date of service 408 may further include other applicable dates. The carrier claim 402 may include information about what dates the patient was unable to work in his or her current occupation, dates of hospitalization related to the current services, charges made to an outside lab in relation to the current services, and so forth. The carrier claim 402 may include information about a referring provider or other source, such as the referring provider's individual NPI. The billing code 412 may include a diagnosis code or an indication of the nature of illness or injury and may further include a CPT or HCPCS code indicating the procedures, services, or supplies used in connection with the billed claim. For each billing code 412 listed in the carrier claim 402, there is also an indication of the date of service, the place of service, the diagnosis pointer, the charges, the days or units, and the rendering provider's practitioner ID 104 for that service, procedure, or supply. The carrier claim 402 may further include a federal tax ID number for the practitioner 102, a patient account number relating to the practitioner's practice, a total charge and the amount paid. The carrier claim 402 additionally includes information on the facility where the service, procedure, or supply was administered to the patient. The information on the facility may include the name, address, contact information, or a clinic ID 108 or facility ID 112 related to the facility.

Facility claims 404 may include additional information not illustrated in FIG. 4. The facility claims 404 may include all the information listed above with reference to the carrier claims 402. The facility claims 404 may additionally include information on when the patient was admitted to the facility, the condition codes pertaining to why the patient was admitted to the facility, and the dates the patient was in-patient or out-patient at the facility. The facility claim 404 may include numerous practitioner IDs 104 pertaining to each of the numerous practitioners 102 who assisted in the patient's care while the patient was at the facility 110. Each service, procedure, or supply administered to the patient during the patient's stay at the facility 110 may linked to a certain practitioner 102.

Figure 5:
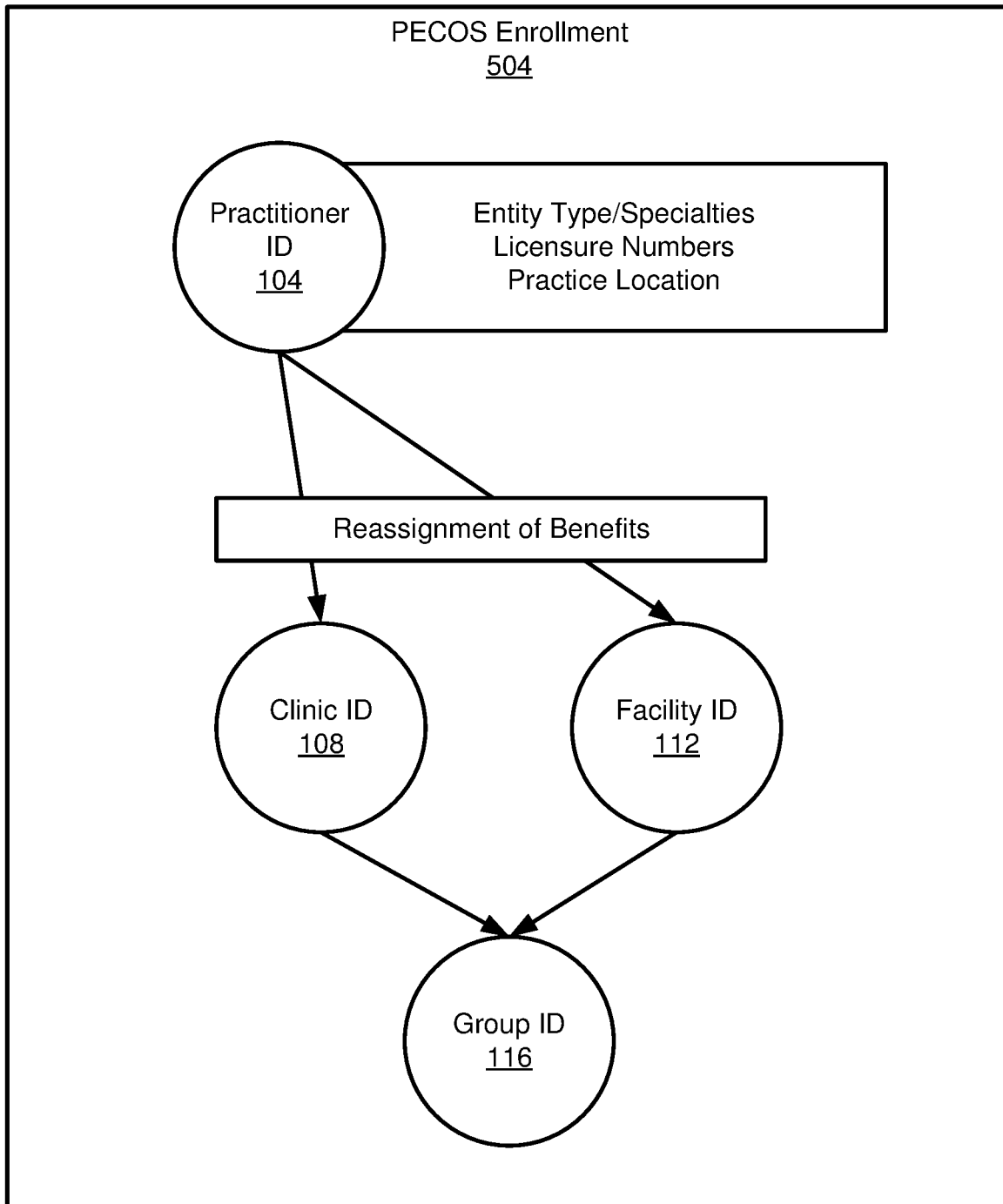
FIG. 5 is a diagram of a file organization schematic for Provider Enrollment, Chain and Ownership System (PECOS) enrollment data.

FIG. 5 is a schematic diagram of PECOS enrollment 504 information relationships. In the United States, the PECOS is used to track the status of healthcare practitioners, and the relationships those healthcare practitioners have with other entities, such as clinics 106, facilities 110, and groups 114. In the PECOS, a practitioner 102 is assigned a practitioner ID 104 in the form of an individual NPI. Additionally, other entities are assigned identification numbers. A clinic 106 is assigned a clinic ID 108 in the form of an organization NPI. A facility 110 is assigned a facility ID 112 in the form of a CMS Certification Number (CCN). A group 114 is assigned a group ID 116 in the form of a PAC ID.

Within PECOS, a practitioner 102 can assign rights to another entity, such as a clinic 106, facility 110, and/or group 114 by storing a reassignment file that links the practitioner's 102 practitioner ID 104 to the clinic ID 108, the facility ID 112, and/or the group ID 116, as applicable. The practitioner 102 can enroll under another entity, such as the clinic 106, the facility 110, and/or the group 114. The practitioner 102 can submit an indication to PECOS that the practitioner 102 is professionally associated with a clinic 106, facility 110, and/or group 114.

In an example, a practitioner is an emergency medicine physician employed by a hospital. The physician is enrolled in PECOS and supplies an individual NPI, assigned previously by the National Plan and Provider Enumeration System (NPPES). A PECOS Associate Control (PAC) ID is assigned to the practitioner, and an enrollment ID is assigned to each of the practitioner's enrollments. Additionally, the hospital is enrolled in PECOS as a facility and supplies an NPI previously assigned. A PECOS Associate Control (PAC) ID is assigned to the facility, and an enrollment ID is assigned to each of the facility's enrollments. The physician may indicate within PECOS that the physician has assigned rights to the hospital, or that the physician is otherwise associated with the hospital, by linking one or more of his or her enrollment IDs with one or more enrollment IDs of the hospital in a reassignment file.

The PECOS enrollment 504 information is not always accurate. The enrollment information within PECOS is often stale with respect to real-world relationships. For example, a practitioner may transition from being employed by a hospital to operating as a sole proprietor. This change is reflected in PECOS only if the practitioner or some other entity indicates within PECOS that the change has occurred. In such an instance, PECOS is not reliable to indicate the real-world professional relationships for that practitioner. In such an instance, the carrier claims submitted by the practitioner can be analyzed in lieu of the information in PECOS, and the analysis gleaned from the carrier claims can be used to override the information in PECOS to identify the practitioner's real-world relationships.

Figure 6A:
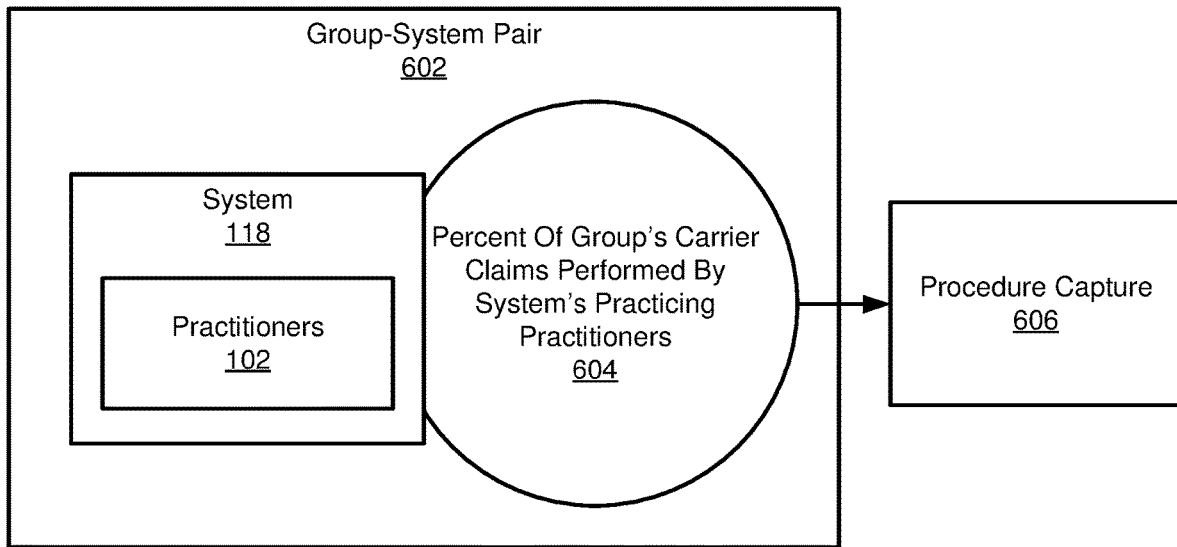
FIG. 6A is a schematic diagram of a data flow for calculating a procedure capture metric based on billed carrier claims under a group-system pair.
Figure 6B:
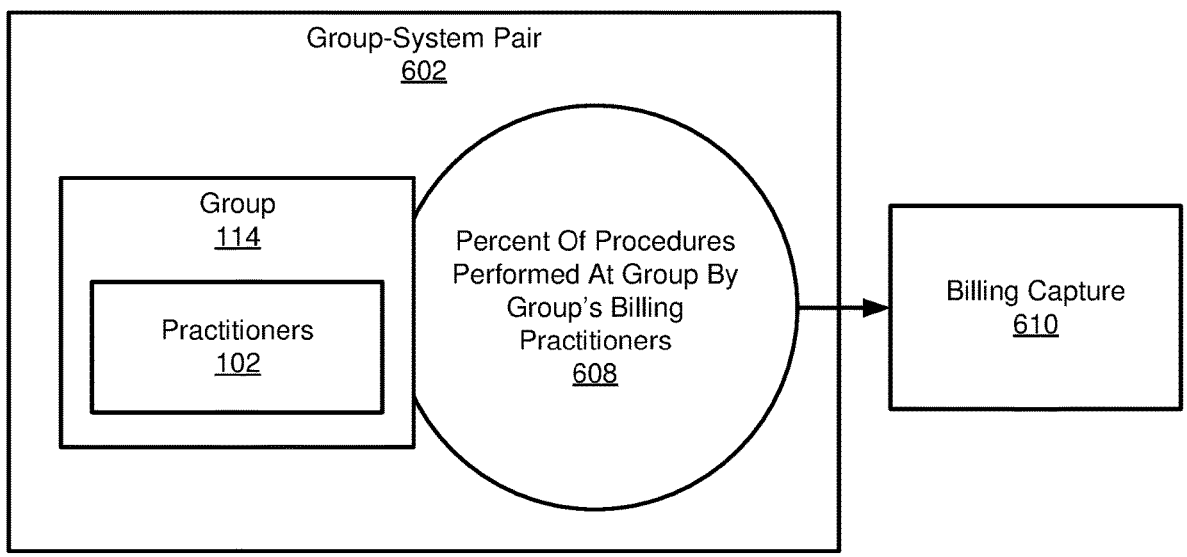
FIG. 6B is a schematic diagram of a data flow for calculating a billing capture metric based on billed carrier claims under a group-system pair.

FIGS. 6A-6B are schematic diagrams of data flows for calculating cohesion metrics that quantify relationships between healthcare entities. These data flows can be used to identify relationships between groups 114 and systems 118. These relationships can extend to other healthcare entities falling under the umbrella of groups 114 and system 118. For example, a relationship may be established between a clinic 106 (under the group 114 umbrella) and a system 118 because a practitioner is billing carrier claims under the clinic 106 and is additionally performing procedures at a facility 110 associated with the system 118. Various cross-relationships between procedure billing 122 entities (i.e., systems 118 and facilities 110) and office billing 126 entities (i.e., groups 114 and clinics 106) can be identified based on the data flows illustrated in FIGS. 6A and 6B. FIG. 6A is a schematic diagram of a data flow diagram for calculating a procedure capture 606 rate and FIG. 6B is a schematic diagram of a data flow for calculating a billing capture 610 rate.

Groups 114 and clinics 106 can be thought of as "capturing" the practitioners 102 who practice at or are employed by a facility 110 or system 118. Through procedure capture 606 measures from the facility 110 and/or system 118 perspective, it can be quantified whether the system 118 and/or facility 110 is operating with a small number of large groups 114 and/or clinics 106, or whether the system 118 and/or facility 110 is operating with a greater number of relatively small groups 114 and/or clinics 106. From the group 114 perspective, the procedure capture 606 metrics can identify the extent to which the group 114 captures a system 118.

The group-system pair 602 discussed in FIGS. 6A and 6B and throughout this document may alternatively and generically be referred to as an "office-procedure pair" herein. The office-procedure pair may be created based on the existence of a common practitioner. The common practitioner is a practitioner that bills carrier claims under a certain office billing identifier 128 and is also associated with facility claims comprising a certain procedure billing identifier 124. The common practitioner may, for example, bill carrier claims comprising a certain clinic identifier 108 and may further perform procedures billed with facility claims comprising a certain facility identifier 112. Additionally, the carrier claims and facility claims associated with the common practitioner may include group identifiers 116 or system identifiers 120. The common practitioner may be identified based on billing carrier claims with an office billing identifier 128 (i.e. a clinic identifier 108 and/or a group identifier 116) and further performing procedures billed on a facility claim comprising a procedure billing identifier 124 (i.e., a facility identifier 112 and/or a system identifier 120). The office-procedure pair is a broader, generic term for a group-system pair 602. The office-procedure pair includes group-system pairs 602, clinic-facility pairs, clinic-system pairs, facility-group pairs, and so forth. The office-procedure pair matches an office billing identifier 128 with a procedure billing identifier 124 to signify a relationships between an office billing 126 entity and a procedure billing 122 entity.

The procedure capture 606 rate is calculated by first creating a group-system pair 602 based on practitioner IDs 104 billing under the group 114 and performing procedures at the system 118. After creating the group-system pair 602, the percent of the group's 114 carrier claims 402 performed by the system's 118 practicing practitioners 102 is calculated at 604. This results in the procedure capture 606 metric.

The billing capture 610 metric has similarities to the procedure capture 606 metric. The billing capture 610 metric can be calculated based on a group's 114 capture of the procedures performed by a practitioner 102 at one of the clinics 106 falling under the group 114. This is the billing capture 610 metric. The billing capture 610 metric is similarly calculated by first creating a group-system pair 602. After the group-system pair 602 is organized, the percent of procedures performed at the group 114 by the group's 114 billing practitioners 102 is calculated at 608.

Figure 7:
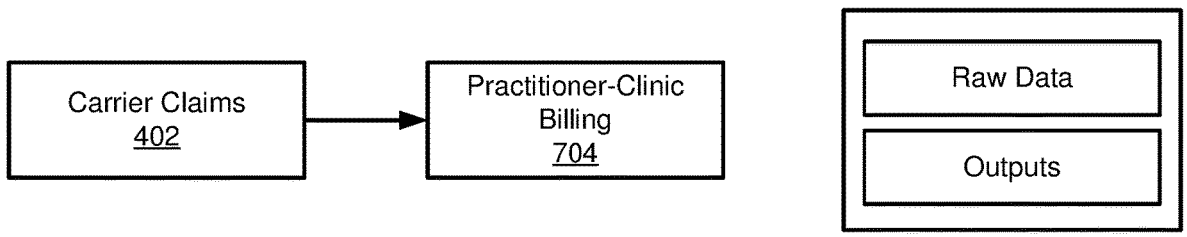
FIG. 7 is a data flow chart for identifying and quantifying a practitioner-clinic billing relationship.

FIG. 7 is a schematic diagram of a data framework for identifying a billing relationship between a practitioner 102 and a clinic 106. The analysis described in connection with FIG. 7 can be used to determine at what clinic(s) 106 a practitioner 102 is billing for services. The billing relationship between practitioners 102 and clinics 106 is based on office-based carrier claims 402. In the United States, when a practitioner 102 bills Medicare for office-based services, a clinic ID 108 is provided on the carrier claim 402. The practitioner-clinic billing 704 relationship may be analyzed and quantified based on the data associated with carrier claims 402. The practitioner-clinic billing 704 relationship is measured by calculating the percentage of a practitioner's 102 total office-based claims that are billed under the clinic ID 108 associated with the clinic 106. If a practitioner 102 bills more frequently under a first clinic than a second clinic, the practitioner 102 is more strongly affiliated with the first clinic.

Figure 8:
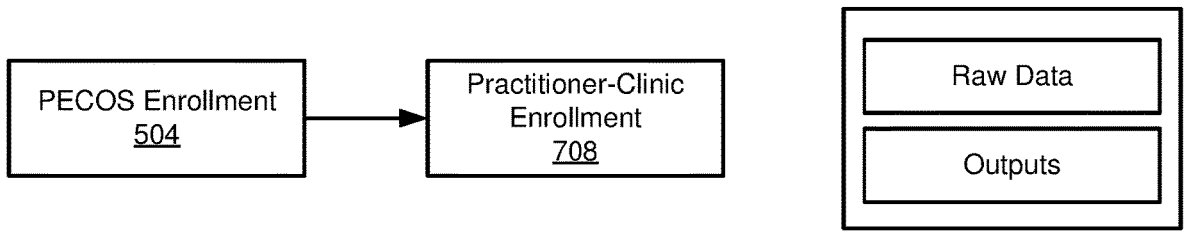
FIG. 8 is a data flow chart for identifying and quantifying a practitioner-clinic enrollment relationship.

FIG. 8 is a schematic diagram of a dataflow for identifying an enrollment relationship between practitioners 102 and clinics 106. The analysis described in connection with FIG. 8 can be used to determine under what clinic(s) 106 the practitioner 102 is enrolled. This is referred to as the practitioner-clinic enrollment 708 relationship. In the United States, individuals and organizations participating in Medicare enroll in PECOS (Provider Enrollment and Chain/Ownership System). PECOS is a system by which practitioners 102 can enroll in the Medicare healthcare system in the United States. A practitioner 102 may enroll under PECOS using a practitioner ID 104 and may designate enrollment under one or more clinic IDs 108 associated with clinics 106 or other organizations. When a practitioner 102 enrolls in PECOS, the practitioner 102 is assigned a group ID 116 and/or system ID 120 (in some embodiments, the group ID 116 and the system ID 120 are the same identifier because the group and system are the same entity) which serves as a unique individual professional identification for interactions with PECOS enrollment 504.

When a practitioner ID 104 or a clinic ID 108 is enrolled in PECOS enrollment 504, the NPI is assigned a unique enrollment identification (ID). An enrollment ID can be used by a practitioner 102 to reassign billing rights to an organization enrollment. A reassignment constitutes an enrollment relationship between a practitioner 102 and an organization such as a clinic 106. Further in the Medicare systems in the United States, each clinic 106 is enrolled under a group ID 116 and/or system ID 120. Because each clinic 106 is associated with a PAC ID, and the PAC ID is additionally associated with a group or system, the enrollment relationship between practitioners 102 and clinics 106 rolls up to groups 114 and systems 118 that are associated with PAC IDs.

A practitioner 102 may reassign to multiple organization enrollments under different group IDs 116 and/or system IDs 120. In practice, these enrollments are sometimes retained after a practitioner transitions to a new practice or clinic 106. Because some enrollments may be "stale" and may no longer reflect the practitioner's 102 actual real-world associations, some enrollments may be discarded. Further, some enrollments may be used only infrequently. This may be the case when, for example, a practitioner 102 who reassigned rights to a specific clinic or group to have the ability to perform procedures for particular patients. In current Medicare systems in the United States, there is no information available on how frequently an enrollment relationship is used by a practitioner 102 other than through billing relationships as discussed in connection with FIG. 7. For this reason, enrollment relationships may be used only to roll clinic 106 locations up to groups 114 or systems 118 when necessary.

In an embodiment, an enrollment relationship between a practitioner 102 and a clinic 106 is identified by retrieving distinct practitioner ID 104 and clinic ID 108 relationships from enrollment and reassignment files over time. This analysis can result in determining a practitioner enrollment metric and a clinic enrollment metric. The practitioner enrollment metric identifies one or more clinics 106 at which a practitioner 102 in enrolled in Medicare in the United States. The clinic enrollment metric identifies one or more practitioners 102 that have enrolled in Medicare under a certain clinic 106.

Figure 9:
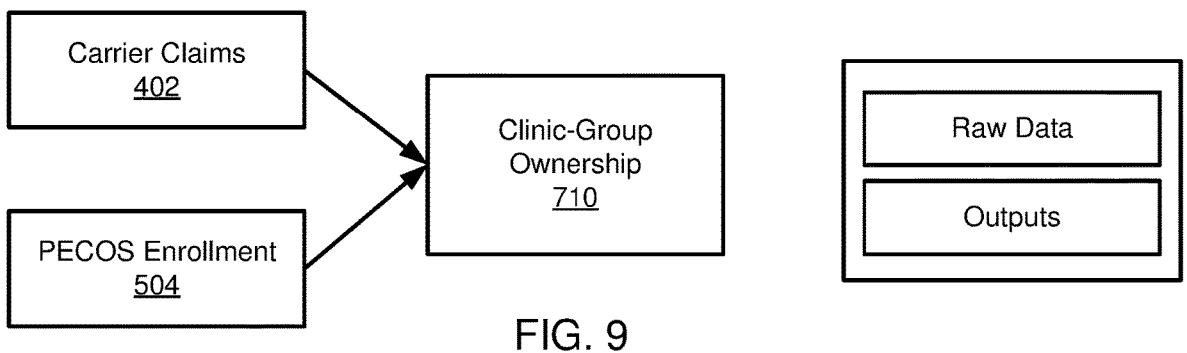
FIG. 9 is a data flow chart for identifying and quantifying clinic-group ownership relationship.

FIG. 9 is a schematic diagram of a data flow for analyzing ownership relationships between clinics 106 and groups 114. The analysis discussed in connection with FIG. 9 can be used to identify group(s) 134 that own one or more clinics 106. This is referred to as the clinic-group ownership 710. In the framework 100 described herein, clinics 106 are owned by groups 114. A group 114 is represented by a group ID 116. In many cases, a clinic ID 108 associated with a clinic 106 appears in an enrollment file for the group 114 with the group ID 116 stated explicitly.

In some cases, the clinic ID 108 for a clinic 106 is not included in PECOS enrollment 504. In these cases, a group ID 116 may be inferred based on enrollment relationships of practitioners 102 to clinics 106. In an embodiment, when more than 50% of practitioners 102 (weighted by the practitioners 102 billing relationship to the clinic 106) enroll under a group ID 116, that group ID 116 is imputed to the owner of the clinic ID 108 for the clinic 106. Alternatively, a group ID 116 may be imputed to the owner of the clinic ID 108 for the clinic 106 if the group ID's 116 squared proportion of provider enrollments exceeds 50% of the sum of the squared proportions of all enrollments for the clinics' 106 billing practitioners 102 (weighted by the practitioners 102 billing relationship to the clinic 106). A portion of these cases have a perfect ownership relationship wherein all billing practitioners reassign to the same group ID 116. In some cases, a clinic 106 has less than perfect ownership when the group ID 116 is imputed to the clinic 106.

In an embodiment, the clinic-group ownership 710 is determined based on carrier claims 402 and data retrieved from the PECOS enrollment 504. In some cases, the clinic ID 108 for the clinic 106 may be identified based on clinic enrollment to retrieve the group ID 116. Where no enrollment exists for the clinic 106, a method includes using reassignments indicated in PECOS enrollment 504 of the practitioners 102 to impute a group ID 116 to the clinic 106. In an embodiment, the reassigned group IDs 116 for practitioners 102 billing carrier claims 402 under a clinic ID 108 are identified using the enrollment and reassignment files. The proportion of all clinic ID 108 and group ID 116 combinations represented by each combination are calculated. The proportions may be weighted by the practitioner's 102 billing relationships and by the number of claims a practitioner 102 bills at the clinic 106. The level of concentration each practitioner 102 shares with each clinic ID 108 is calculated by taking the sum of the squared proportions.

In an embodiment, a certain group ID 116 and clinic ID 108 combination is selected if the combination has more than 50% of the reassignments of the clinic's 106 practitioners. This can be determined by using the enrollment and reassignment files to identify the reassigned group IDs 116 of practitioners 102 who bill carrier claims 402 under a clinic ID 108. In an embodiment, a certain group ID 116 and clinic ID 108 combination is selected if the combination has a squared proportion greater than 50% of the concentration of a practitioner's 102 shares within the clinic 106. This can be calculated by taking the sum of the squared proportions as done in the Herfindahl-Hirschman Index (HHI).

The metrics pertaining to the clinic-group ownership 710 include practitioner group billing and group billing. The practitioner group billing is the proportion of the practitioner's 102 carrier claims 402 billed under any of a group's 114 clinics 106. The group billing is the proportion of all carrier claims 402 billed under any of the group's 114 clinics 106 that were performed by a specific practitioner 102.

Figure 10:
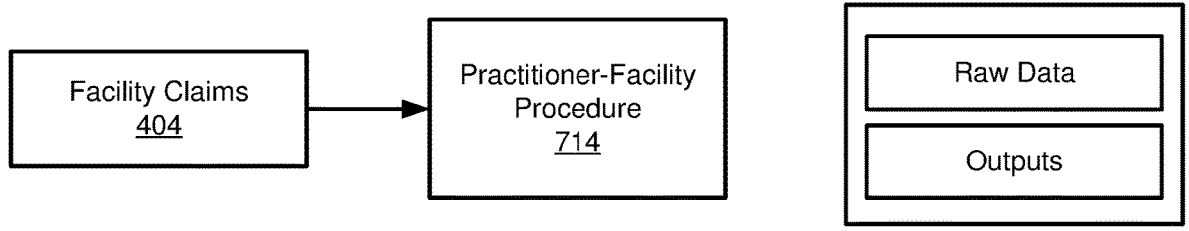
FIG. 10 is a data flow chart for identifying and quantifying a practitioner-facility procedure relationship.

FIG. 10 is a schematic diagram of a method for identifying and quantifying the practitioner-facility relationship with respect to procedures. The analysis discussed in connection with FIG. 10 can be used to determine at what facilities 110 a practitioner 102 is performing procedures. This is referred to as the practitioner-facility procedures 714 metric. When a practitioner 102 performs a procedure at a facility 110, a facility claim 404 is submitted that includes the practitioner's 102 practitioner ID 104, and clinic ID 108 for an associated clinic 106, and a CMS Certification Number (facility ID). In some embodiments, the facility ID 112 is a CMS provider number. The proportion of procedures performed by a practitioner at a certain facility 110 is quantified based on the relationship in the claims between practitioner IDs and facility IDs. Further, the proportion of the facility's 110 procedure volume that were performed by a certain practitioner 102 is quantified based on the relationship in the claims between practitioner IDs 104 and facility IDs 112. These procedure volumes provide a link between practitioners 102 and facilities 110 apart from any official ownership or employment relationships.

The raw data input includes all facility claims 404 files such as inpatient, outpatient, hospice, and so forth. The practitioner-facility procedure 714 is determined by identifying the distinct NPIs that participated in each claim. This can be performed for each claim in a given year. Participating entities are denoted in the attending, operating, rendering, and other identifier fields within the facility claims 404. An identifier (e.g., a National Provider Identifier (NPI)) can appear in more than one of these fields and the duplicates should be handled when calculating the practitioner-facility procedures 714 metric. For each pair including a participating practitioner 102 and a facility 110, the number of claims represented by the pair is counted. The claim numbers by distinct pair are summed across all claim files. This process may be repeated for each year of available claims data.

The practitioner-facility procedures 714 metrics results in a practitioner facility procedure volume metric and a facility procedure volume metric. The practitioner facility procedure volume metric is the proportion of a practitioner's total procedure claims performed at a certain facility. A practitioner's procedure claim is a claim in which the practitioner participated in the procedure. The facility procedure volume is the proportion of procedures performed at a certain facility by each of one or more practitioners using the certain facility.

Figure 11:
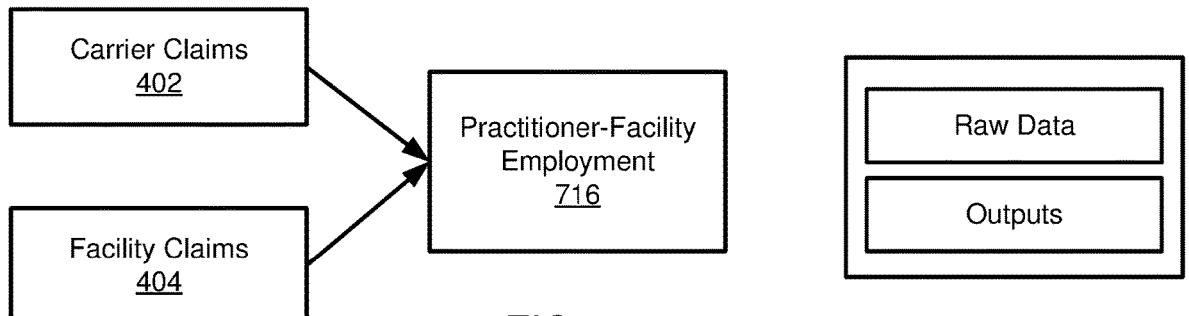
FIG. 11 is a data flow chart for identifying and quantifying a practitioner-facility employment relationship.

FIG. 11 is a schematic diagram of a data flow for identifying employment relationships between practitioners and facilities. The analysis discussed in connection with FIG. 11 can be used to determine what facilities directly employ a practitioner. This is referred to as the practitioner-facility employment 716 metric. When a practitioner is directly employed by a facility, the practitioner's billed claims will likely be processed by the facility. In such an instance, the facility might submit a bill including facility charges and practitioner charges, and the practitioner does not send a separate bill. This billing relationship impacts the dynamic between the practitioner and the facility, and further impacts the dynamics between the practitioner and other entities such as healthcare groups, healthcare systems, health insurance agencies, patients, and so forth. Therefore, it can be important to understand whether a practitioner 102 has a direct employment relationship with a facility 110.

In some cases, a practitioner 102 is employed directly by a facility 110. This is distinct from practitioners 102 who practice exclusively at the facility 110. In an embodiment, to determine employment, office-based claims with facility IDs (Centers for Medicare and Medicaid Services (CMS) Certification Numbers) 112 are matched using a multiple step matching process. The proportion of a practitioner's total carrier claims 402 performed in a facility is calculated based on the result of the multiple step matching process.

In some instances, a practitioner 102 is paid less on an office-based claim if there is a facility fee associated with the claim. This occurs because the facility 110 is also billing for the service. The total of the practitioner's fee and the facility fee in these cases is generally higher than the practitioner's fee would be alone at a non-facility setting. Identifying this scenario can lead to concluding that practitioners 102 billing carrier claims 402 at a facility 110 are employed by the facility. When performing this analysis on typical real-world data, the analysis confirms that a majority of practitioners bill all carrier claims 402 or no carrier claims 402 under a facility 110. In an embodiment, practitioners with claims that are all matched to a facility are deemed employed by that facility.

The practitioner-facility employment 716 determination can be performed based on a claims analysis file. The claims analysis file is generated based on claims analytics and practitioner affiliations. The claims analytics and practitioner affiliations are identified based on billed claims. In an embodiment, the practitioner-facility employment 716 determination is calculated at least in part based on the result of a multiple step data merging process for matching facility claims 404 (facility IDs) to carrier claims 402. The data merging process occurs by attempting to match unmatched carrier claims 402 from a prior step to practitioners using one or more of the following variables. A possible variable is the patient, service data, and HCPCS (Healthcare Common Procedure Coding System) code. The HCPCS code may alternatively be referred to as a "procedure code" herein. A further possible variable is the patient, service date, and practitioner NPI. A further possible variable is the match based on inpatient location if the carrier claim occurs during a hospitalization and is then matched to that facility. A further possible variable is the service date and the practitioner's most common facility. A further possible variable is the most common facility based on the clinic ID in the carrier claim 402. A further possible variable is the service date and the practitioner's most common facility. A further possible variable is the service date and the practitioner's most common facility within a two-week range. A further possible variable is the service date and the practitioner's most common facility. A further possible variable is the practitioner's most common provider within two weeks using the previously joined facilities. A further possible variable is the facility that is most closely attached with the clinic ID from the carrier claim.

In an embodiment, the facility claims 404 (facility IDs accessible via PECOS enrollment 504) are matched to carrier claims 402 using the following 10-step merge process. The merge occurs by attempting to match unmatched carrier claims 402 from the prior step to practitioners 102 using the following variables:

a. Patient, service date, and HCPCS code;
b. Patient, service date, and practitioner's practitioner ID;
c. Inpatient location if the carrier claim occurs during a hospitalization at the facility;
d. Service date and practitioner's most common facility;
e. Most common facility based on the clinic ID in the carrier claim;
f. Service date and the practitioner's most common facility (again);
g. Service date and the practitioner's most common facility within a two-week time period;
h. Service date and the practitioner's most common facility (again);
i. Practitioner's most common provider within two weeks, using the previously joined facilities; and
j. The facility most closely attached to the clinic ID from the carrier claim.

When the data has been merged, a method may further include calculating the percentage of a practitioner's 102 carrier claims 402 that occurred at a facility 110 by collapsing the practitioner's practitioner ID 104 and the facility's clinic ID 108. In an embodiment, carrier claims 402 that have a place of service code equal to eleven (office-based claims) or twenty-two (hospital outpatient department claims) are used to determine employment. The proportion of such claims that have place of service code represents the strength of the practitioner's 102 employment relationship with the facility 110. A method may further include collapsing to the clinic 106 or group 114 level and saving a percent of the group's 114 practitioners 102 that are employed by facilities or systems. This can be performed for all years of available claims.

The merge process for matching carrier claims 402 to a facility 110 and/or facility claims 404 is a novel data manipulation process that is performed on a very large set of data. The number of carrier claims 402, facilities 110, and facility claims 404 can be enormous for a singular calendar year. This number of claims is impossible for a single human or group of humans to process, and particularly within the same calendar year of the billed claims. The merge process is a novel set of rules specifying how carrier claims 402 should be matched to a facility 110 and or to facility claims 404.

In an embodiment, the carrier claims 402, the facility IDs 112, and the facility claims 404 are stored in a database. The data (i.e., the combination of the carrier claims 402, the facility IDs 112, and the facility claims 404) is typically retrieved from larger files or data stores and includes superfluous information that is not necessary for identifying and quantifying the practitioner-facility employment 716 relationship. The data is therefore cleaned prior to storage in the database. The data is cleaned such that 10-step matching process can be performed on a manageable sum of data. In an embodiment, the data is equivalent to about 1 terabyte (TB) of data per claim year.

In an embodiment, the cleaned data is linked to a database platform. The database platform is in communication with a user interface (UI) such that the data can be viewed seamlessly. The data can be partitioned within the database based on calendar year, entity, practitioner 102, facility 110, facility ID 112, carrier claim 402, facility claim 404, and so forth. The database platform is built on highly modeled, as opposed to raw, data sources.

In an embodiment, as information stored in the database is changed, the practitioner-facility employment 716 metric is reevaluated. A change to the information stored in the database may reflect that a new facility 110 is added, a new practitioner 102 is added, there is a new relationship between a practitioner and a facility, there are new claims submitted, and so forth. The practitioner-facility employment 716 metric may be reevaluated to determine whether a new employment relationship has been formed, an employment relationship has been discontinued, or an employment relationship has changed. This reevaluation can be performed in real-time as the data as changed and can therefore provide an up-to-date and reliable representation of the real-world relationships between practitioners and facilities. Conducting this analysis by hand (by the human mind) in real-time would be so impractical that it could be considered impossible.

Figure 12:
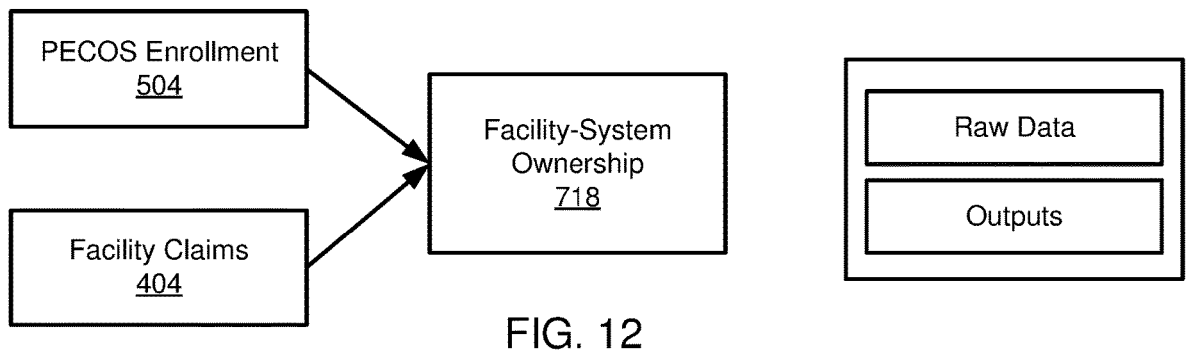
FIG. 12 is a data flow chart for identifying and quantifying a facility-system ownership relationship.

FIG. 12 is a schematic diagram of a data framework for identifying and quantifying the ownership relationship between a facility 110 and a system 118. The analysis described in connection with FIG. 12 can be used to determine what system owns a facility, and which facilities are owned by the system. The resulting metric is referred to as the facility-system ownership 718 metric.

The ownership relationship between a system 118 and one or more facilities 110 can be assessed using the enrollment file and claims-based link between clinic IDs and facility IDs. A facility claim 404 can include clinic IDs 108 and facility IDs 112 for the facilities 110 at which a practitioner 102 performs procedures. The distinct combinations of clinic ID 108 and facility ID 112 allow for a link between these two identifiers. In some instances, multiple clinic IDs 108 roll up to one system ID 120, and this typically indicates a different department within the facility or a change of ownership. In some instances, multiple facility IDs 112 link to the same clinic ID 108, and this typically occurs when a facility 110 makes a transition, such as an acute care hospital gaining critical access status. However, in most instances, clinic IDs 108 and facility IDs 112 match one-to-one. Using all facility ID 112 to clinic ID 108 matches and the PECOS enrollment 504 file (which contains enrollment of clinic IDs 108 under corresponding system IDs 120), a facility ID 112 can be rolled up to a system ID 120 in an ownership relationship. Further research can be performed to identify parent companies.

In an embodiment, the data inputs for identifying the facility-system ownership 718 relationship is the facility claims 404 for a facility 110 and the PECOS enrollment 504 file for the facility 110 and/or system 118. A method for determining the facility-system ownership 718 relationship includes one or more of the following steps. The method includes using the facility claims 404 to match facility IDs 112 to clinic IDs 108 for each claim year. The method includes using enrollment information from the PECOS enrollment 504 file to match clinic IDs 108 to system IDs 120. The method includes handling duplications such as system IDs 120 that may be owned by common parent organizations.

The facility system-ownership 718 relationship can be leveraged to identify multiple metrics, including the practitioner-system employment metric, the practitioner-system procedure volume metric, and the system procedure volume metric. The practitioner-system employment metric is a level of confidence that a practitioner 102 is employed by a system 118. The practitioner-system procedure volume is a proportion of all procedure claims in which the practitioner 102 participated that were performed at the system 118. The system procedure volume is a proportion of all procedures performed at a system 118 in which the practitioner 102 participated.

Figure 13:
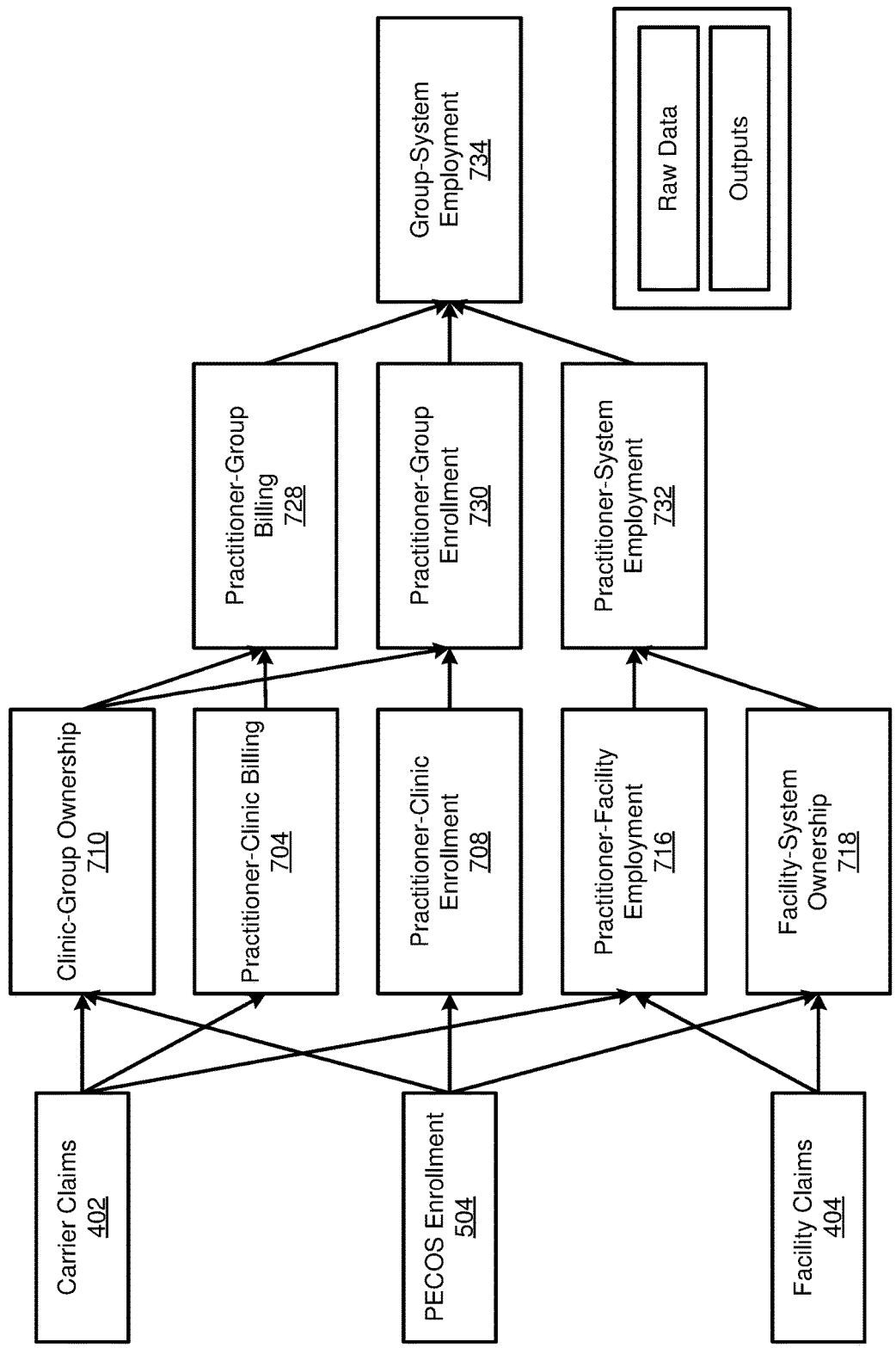
FIG. 13 is a data flow chart for identifying and quantifying a group-system employment relationship.

FIG. 13 is a schematic diagram of a data framework for determining relationships between systems 118 and groups 114. The analysis discussed in connection with FIG. 13 can be used to determine a practitioner-group billing 728 relationship, a practitioner-group enrollment 730 relationship, a practitioner-system employment 732 relationship, and/or a group-system employment 734 relationship.

In some embodiments, groups 114 and systems 118 are treated as separate entities for purposes of the analyses described herein. However, in some cases, a system 118 and a group 114 may be the same entity. This is indicated by a system and a group sharing a common identifier. When implemented in the United States, the group ID 116 and the system ID 120 may be the same PAC ID. The idea for other relationships between systems 118 and groups 114 discussed herein can be calculated regardless of any identity relationships between the systems and groups. Therefore, even if a group 114 and a system 120 share a PAC ID, the relationships discussed herein can still be calculated.

In some instances, systems 118 and groups 114 can have a number of different relationships to other systems and groups based on their relationships to individual practitioners 102, facilities 110, and clinics. For example, if a group 114 has a high percentage of billing practitioners 102 employed by a facility 110 within a system 118, the group 114 can be designated as being employed to some extent by the facility 110 or system 118. This link can be identified by performing an employment analysis and rolling the employment analysis up to a group 114 level using practitioner 102 billing and reassignment. When the employment analysis is rolled up, the percent of the group 114 employed by the facility 110 or system 118 can be calculated.

The analysis surrounding the group-system employment 734 relationship can yield multiple metrics, including the group-facility employment metric and the group-system employment 734 metric. The group-facility employment metric is the percent of a group's 114 enrolled practitioners 102 that are employed by a facility 110 falling under the system 118 of the group-system pair 602. The group-system employment 734 metric is the percent of a group's 114 enrolled practitioners 102 that are employed by the system 118 of the group-system pair 602.

Figure 14:
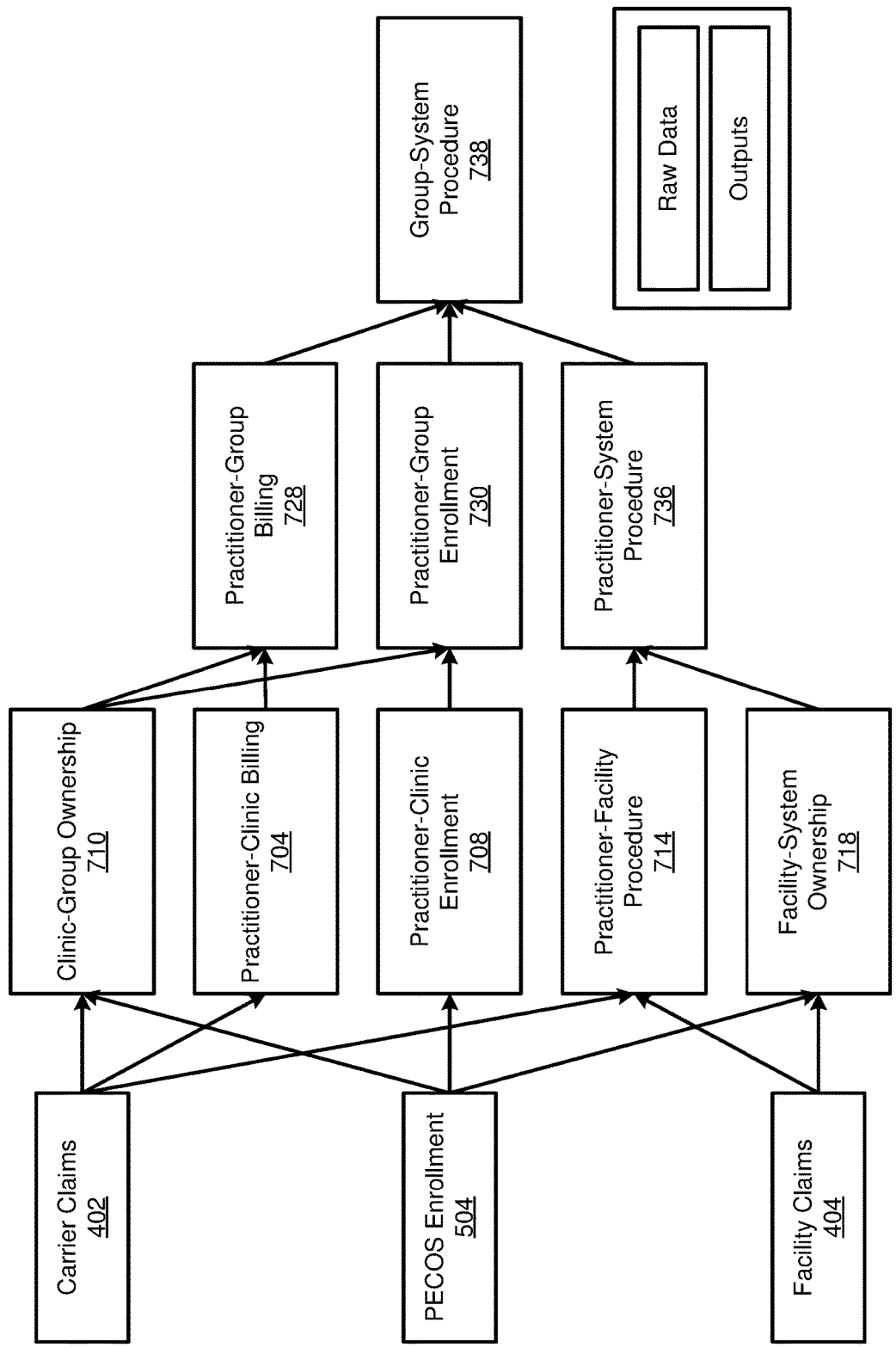
FIG. 14 is a data flow chart for identifying and quantifying a group-system procedure relationship.

FIG. 14 is a schematic diagram of a data framework for identifying and quantifying relationships between groups 114 and systems 118. The analysis in connection with FIG. 14 can be used to determine the group-system procedure 738 relationship. In some implementations, it is beneficial to know the percentage of procedures performed by a group's 114 practitioners 102 that are performed at a facility 110 or system 118. This determination can be calculated as a roll-up of the practitioner-facility procedure 714 analysis discussed in FIG. 10. The data framework illustrated in FIG. 14 is similar to the schematic diagram shown in FIG. 13. However, FIG. 14 illustrates facility claims 404 that are used to calculate metrics including practitioner-facility procedure 714, which is used to calculate practitioner-system procedure 736 and ultimately the group-system procedure 738 relationship. Whereas FIG. 13 uses facility claims 404 to calculate practitioner-facility employment 716, which is used to calculate practitioner-system employment 732 and ultimately the group-system employment 734 relationship.

The group-system procedure 738 relationship can yield multiple metrics, including the group-facility procedure volume metric and the group-system procedure volume metric. The group-facility procedure volume metric is the proportion of procedures performed by a group's 114 billing practitioners 102 at a given facility 110. The group-system procedure 738 volume is the proportion of procedures performed at a system's 118 facilities 110 by a group's 114 billing practitioners 102.

Figure 15:
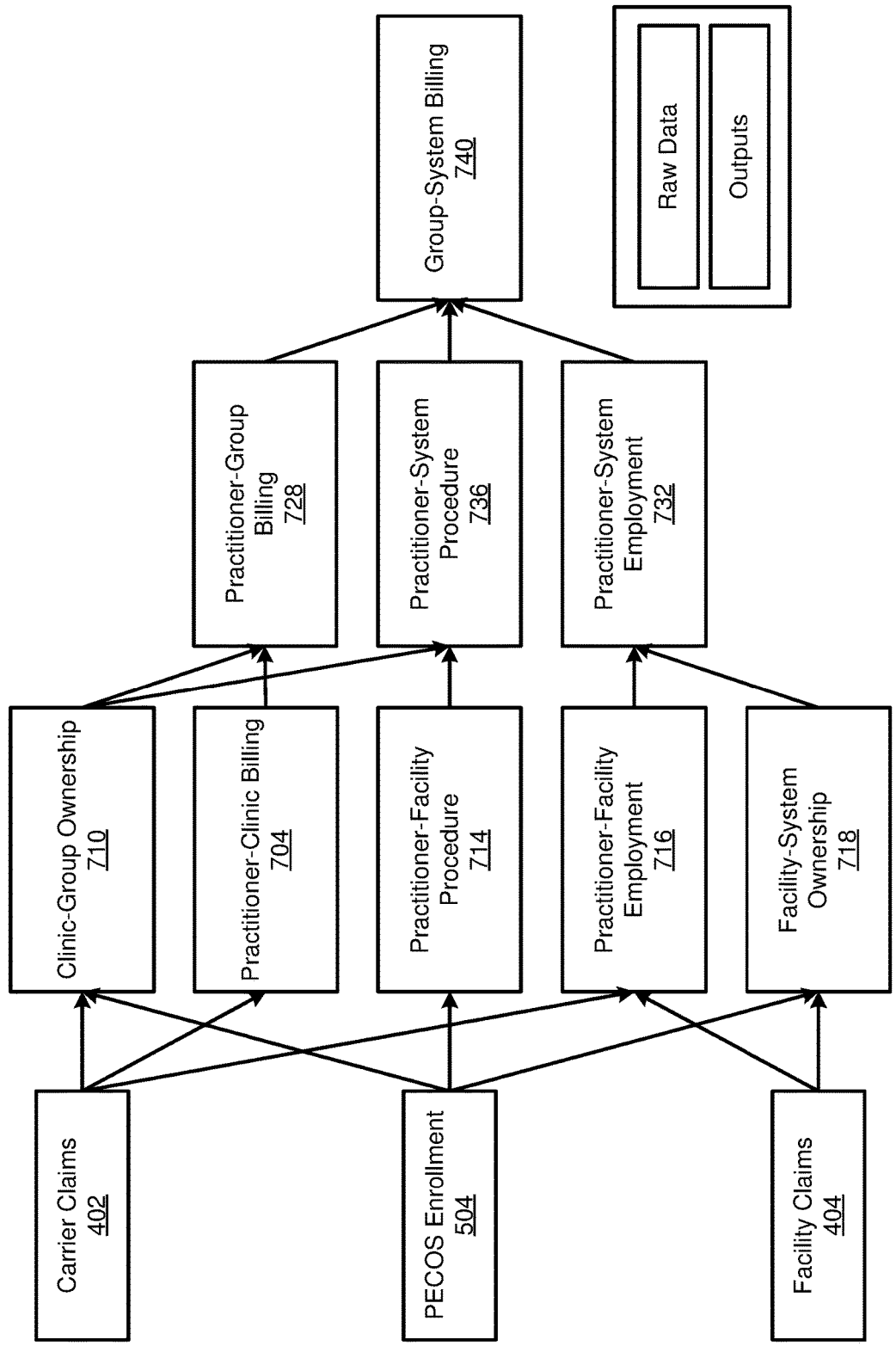
FIG. 15 is a data flow chart for identifying and quantifying a group-system billing relationship.

FIG. 15 is a schematic diagram of a framework for identifying and quantifying billing relationships between a group 114 and a system 118. The analysis discussed in connection with FIG. 15 can be used to determine the group-system billing 740 relationship. Rolling up the billing affiliations of practitioners 102 employed by or performing procedures at a facility 110 or system 118 may allow for examination of the group 114 as a system 118 that predominantly employs the practitioners 102. In an embodiment, this is calculated as the inverse of the group-system employment 734 relationship and/or the group-system procedure 738 relationship. The data framework illustrated in FIG. 15 is similar to the schematic diagram shown in FIG. 14. However, FIG. 15 illustrates facility claims 404 that are used to calculate metrics including practitioner-facility employment 716, which is used to calculate practitioner-system employment 732 and ultimately the group-system billing 740 relationship. Whereas FIG. 14 uses facility claims 404 to calculate practitioner-facility procedure 714, which is used to calculate practitioner-system procedure 736 and ultimately the group-system procedure 738 relationship.

The group-system billing 740 relationship can yield multiple metrics, including the facility billing metric, the system billing metric, the facility-employed-practitioner billing metric, and the system-employed-practitioner billing metric. The facility billing metric is the proportion of practitioners 102 performing procedures at a facility 110 who have a billing relationship with a group 114, weighted by the strength of the practitioners' 102 billing relationships. The system 118 billing metric is the proportion of practitioners 102 performing procedures at a system 118 who have a billing relationship with a group 114, weighted by the strength of the practitioners' 102 billing relationships. The facility-employed-practitioner billing metric is the proportion of practitioners 102 employed by a facility 110 who have billing relationships with a group 114, weighted by the strength of the practitioners' 102 billing relationships. The system-employed-practitioner billing metric is the proportion of practitioners 102 employed by a system 118 who have billing relationships with a group 114, weighted by the strength of the practitioners' 102 billing relationships.

Figure 16:
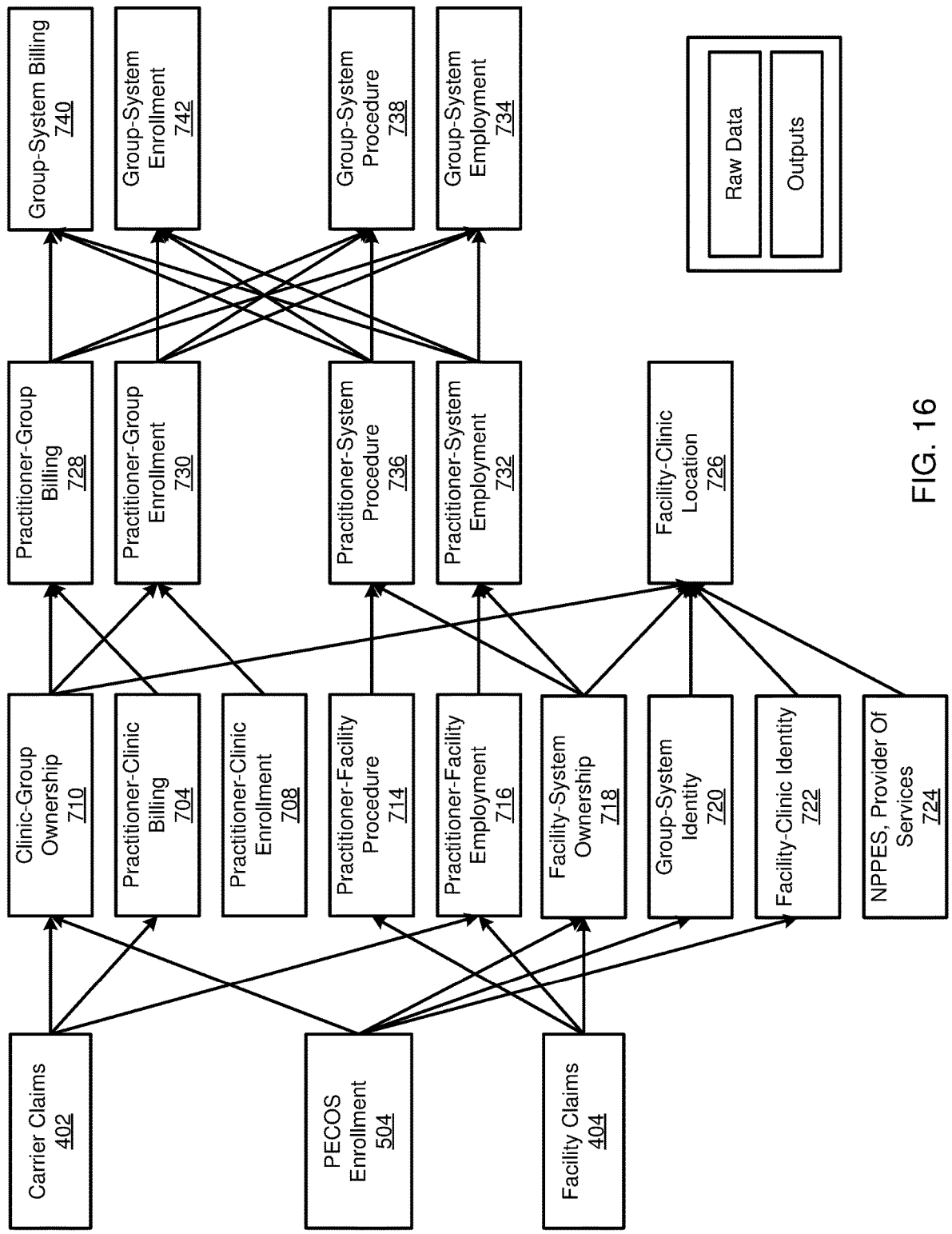
FIG. 16 is a data flow chart for identifying and quantifying a group-system billing relationship, a group-system enrollment relationship, a group-system procedure relationship, and/or a group-system employment relationship.

FIG. 16 is a schematic diagram of a data framework for quantifying cohesion between clinics 106 and groups 114. The analysis discussed with respect to FIG. 16 can be used to quantify group-system billing 740 relationships, group-system enrollment 742 relationships, group-system procedure 738 relationships, and/or group-system employment 734 relationships. FIG. 16 also illustrates that PECOS enrollment 504 can be used to calculate metrics including group-system identity 720, and facility-clinic identity 722, which is used with other metrics, including data from NPPES 724, to calculate facility-clinic location 726.

The cohesion of a clinic's 106 billing practitioners 102, and the cohesion of a group's 114 billing practitioners 102, can be assessed based on billing relationships of practitioners 102 to clinics 106 and/or groups 114. In some instances, it is beneficial to know if a practitioner 102 bills exclusively to a certain clinic 106 or group 114, or if the practitioner 102 also bills to other clinics 106 or groups 114. It can further be beneficial to identify all clinics 106 and groups 114 that a practitioner 102 bills to, and the proportion of the practitioner's 102 bills that are sent to each clinic 106 or group 114.

In an embodiment, clinic-group billing cohesion is determined by employing a method that includes one or more of the following steps. The method includes identifying practitioners 102 billing carrier claims 402 under each of one or more group IDs 116. The data can be assessed to identify which group IDs 116 a practitioner 102 bills to and to quantify the total carrier claims 402 billed to each group ID 116. The method may include saving the practitioner-group pairings and collapsing to one row per group 114. The method may include calculating summary metrics for each group 114 from the group's 114 perspective. Summary metrics may include HHI of shares as the sum of squared shares within the target group ID 116, and the percent of carrier claims 402 that target the group's 114 practitioners 102 billed under the target group ID 116 itself. This can be performed for all years of available claims.

The group cohesion analysis can yield multiple metrics, including the clinic practitioner-billing cohesion metric, the group-practitioner billing cohesion metric, the clinic-billing cohesion metric, and the group-billing cohesion metric. The group-practitioner cohesion metric measures the cohesion of a group's 114 billing practitioners 102. The group-practitioner cohesion metric can be used to determine what proportion of the group's 114 practitioners 102 are billing to the group 114 and/or a clinic 108 associated with the group 114. The group-practitioner cohesion metric can be used to determine what proportion of the group's 114 practitioners 102 are billing to other clinics 108 or groups 114, and to which other clinics 108 and groups 114 those practitioners 102 are billing.

FIG. 16 further illustrates relationships between facilities 110 and systems 118 that can be assessed for calculating facility-system procedure cohesion. The cohesion of practitioners 102 that practice at facilities 110 and systems 118 can be calculated based on procedure relationships between the practitioners 102 and the facilities 110 and/or systems 118. The overall cohesion score can be calculated as an HHI-type measurement. The overall cohesion score indicates how fully the system 118 or facility 110 is capturing its affiliated practitioner's 102 procedure work. In an instance where a practitioner 102 is employed by a facility 110 or system 118, an overall cohesion score can still be calculated for that practitioner 102 and facility 110 or system 118. These cohesion metrics can be rolled up to the group 114 level to determine how cohesive the system 118 or facilities 110 practicing or employing clinics 106 or groups 114 are.

In an embodiment, the facility-system procedure cohesion metrics can be calculated by employing a method including one or more of the following steps. The method may include identifying practitioners 102 billing facility claims 404 under a certain system ID 120. This step may include identifying what system IDs 120 the practitioner 102 is performing procedures at and then sharing the total facility claims 404 identifying each system ID 120. The method may include saving the practitioner-system/facility pairings and then collapsing to one row per system or facility. The method may include calculating summary metrics for each system 118 or facility 110 from the system's or facility's perspective. The summary metrics may include HHI of shares as the sum of squared shares within the target system ID 120 and the percent of facility claims 404 the target system's 118 practitioners 102 performed at the target system 118 itself. This method can be performed for all years of available claims.

The facility or system procedure cohesion analysis can yield multiple metrics, including the facility-practitioner procedure cohesion metric, the system-practitioner procedure cohesion metric, the facility-procedure cohesion metric, and the system-procedure cohesion metric. The facility-practitioner procedure cohesion metric is the proportion of claims performed at a certain facility 110 by a practitioner 102 who performed any claims at the facility 110. The system-practitioner procedure cohesion metric is the proportion of claims performed at a system's 118 facilities 110 by a practitioner 102 who performed any claims at the system's 118 facilities 110. The facility-procedure cohesion metric is the sum of the squared facility-practitioner cohesion metrics for the facility 110. The system-procedure cohesion metric is the sum of the squared system-practitioner cohesion metrics for the system 118.

Groups 114 and clinics 106 can be thought of as "capturing" practitioners 102 who practice at or are employed by a facility 110 or system 118. Through billing capture measures from the facility 110 or system 118 perspective, it can be determined whether the system 118 or facility 110 is working with a handful or large groups 114 of clinics 106, or if the system 118 or facility 110 is working with a larger number of relatively small groups 114 or clinics 106. Further, it can be determined from the group's 114 or clinic's 106 perspective the extent to which the group 114 or clinic 106 captures a system 118.

In an embodiment, billing capture relationships can be determined by performing one or more of the following steps. A method may include creating a group-system pair 602 based on individual NPIs billing under the group 114 and performing procedures at the system 118. The method may include calculating the percent of all the group's 114 carrier claims 402 that were performed by the system's practicing providers weighted by the procedure affiliation with the system. The method may include calculating the percent of all carrier claims 402 billed by the system's practitioners that were billed under the group and weighted by procedure affiliation. The method may include saving each of a plurality of group-system pairs and generating a summary file for each system and each group. This may further include calculating summary metrics for the system including the system's capture HHI sum of squared shares of system procedures. This may further include calculating summary metrics for the group that include the group's capture HHI sum of squared shares of the group's procedures. The aforementioned method steps can be performed for all years of available claims.

Assessing the group-system capture relationship can yield multiple metrics, including the group-facility billing capture metric, the group-system billing capture metric, the facility-group billing capture metric, the system-group billing capture metric, the group-facility billing capture score, the group-system billing capture score, the facility-group billing capture score, and the system-group billing capture score. Analogous metrics involving groups 114 may also be calculated, wherein these metrics are based on practitioners 102 billing to clinics 108 associated with the group 114 rather than based on practitioners 102 billing to facilities 110 under the system 118. The group-facility billing capture metric is the proportion of carrier claims 402 billed under the group by practitioners who performed procedures at the facility. The group-system billing capture metric is the proportion of carrier claims 402 billed under the group by practitioners who performed procedures at the system. The facility-group billing capture metric is the proportion of carrier claims 402 performed by practitioners who billed under the group out of all carrier claims 402 performed by the facility's performing practitioners. The system-group billing capture metric is the proportion of carrier claims 402 performed by practitioners 102 who billed under the group 114 out of all carrier claims 402 performed by the system's 118 performing practitioners 102. The group-facility billing capture score is the sum of the squared group-facility billing capture metrics for the facility. The group-system billing capture score is the sum of the squared group-system billing capture metrics for the system. The facility-group billing capture score is the sum of the squared facility-group billing capture metrics for the group. The system-group billing capture score is the sum of the squared system-group billing capture metrics for the group.

In an embodiment, it can be beneficial to determine the billing capture 610 for different healthcare entities. As with billing capture, procedure capture calculates metrics for a system's or facility's capture of a group's or clinic's practitioners' procedures. In an embodiment, a method for determining procedure capture metrics includes one or more of the following steps. The method may include creating a group-system pair based on individual NPIs billing under the group and performing procedures at the system. The method may include calculating the percent of all procedures performed at the system that were performed by the group's billing providers weighted by their billing affiliation and number of procedure claims. The method may further include calculating the percent of all procedures performed by the group's 114 billing practitioners 102 that were performed at the system 118 using the same weights. The method may further include saving the group-system pairs 602 and generating summary files for each system 118 and each group 114. The summary files may include summary metrics for the system including the system's 118 capture HHI sum of squared shares of system procedures. The summary files may further include summary metrics for the group including the group's capture HHI sum of squared shares of the group's procedures. The method can be repeated for all years of available claims.

The evaluation of billing capture 610 can yield multiple metrics, including the group-facility procedure capture metric, the group-system procedure capture metric, the facility-group procedure capture metric, the system-group procedure capture metric, the group-facility procedure capture score, the group-system procedure capture score, the facility-group procedure capture score, the system-group procedure capture score, the clinic-practitioner billing cohesion, the group-practitioner billing cohesion, the clinic billing cohesion, the group billing cohesion, the clinic billing metric, the clinic enrollment metric, the clinic procedure cohesion metric, and the group procedure cohesion metric. It should be appreciated that additional metrics may be calculated based on the evaluation of billing capture 610.

The group-facility procedure capture metric is the proportion of all facility claims 404 performed at the facility 110 that were performed by practitioners who billed under the group. The group-system procedure capture is the proportion of all facility claims performed at the system's facilities that were performed by practitioners who billed under the group. The facility-group procedure capture metric is the proportion of all facility claims performed by the group's billing practitioners that were performed at the facility. The system-group procedure capture metric is the proportion of all facility claims performed by the group's billing practitioners that were performed at the system's facilities. The group-facility procedure capture score is the sum of the squared group-facility billing capture metrics for the facility. The group-system procedure capture score is the sum of the squared group-system billing capture metrics for the system. The facility-group procedure capture score is the sum of the squared facility-group billing capture metrics for the group. The system-group procedure capture score is the sum of the squared system-group billing capture metrics for the group.

The clinic-practitioner billing cohesion metric is the proportion of all office billing 126 performed by practitioners with any billing relationship with the facility claims that were billed under the facility. This metric involves carrier claims 402 billed by a clinic 106. Conversely, facility-practitioner procedure cohesion involves facility claims 404 billed by a facility 110. The group-practitioner billing cohesion metric is the proportion of all office billing 126 performed by practitioners with any billing relationship with the group that were billed under the group. The clinic billing cohesion metric is the sum of the squared clinic-practitioner billing cohesion metrics for the clinic. The group billing cohesion metric is the sum of the squared group-practitioner billing cohesion metrics for the group.

The group-practitioner procedure cohesion metric is the proportion of all office claims performed by practitioners with any billing relationship with the group that were billed under the group. Group billing cohesion is the sum of the squared group-practitioner billing cohesion metrics for the group.

Figure 17:
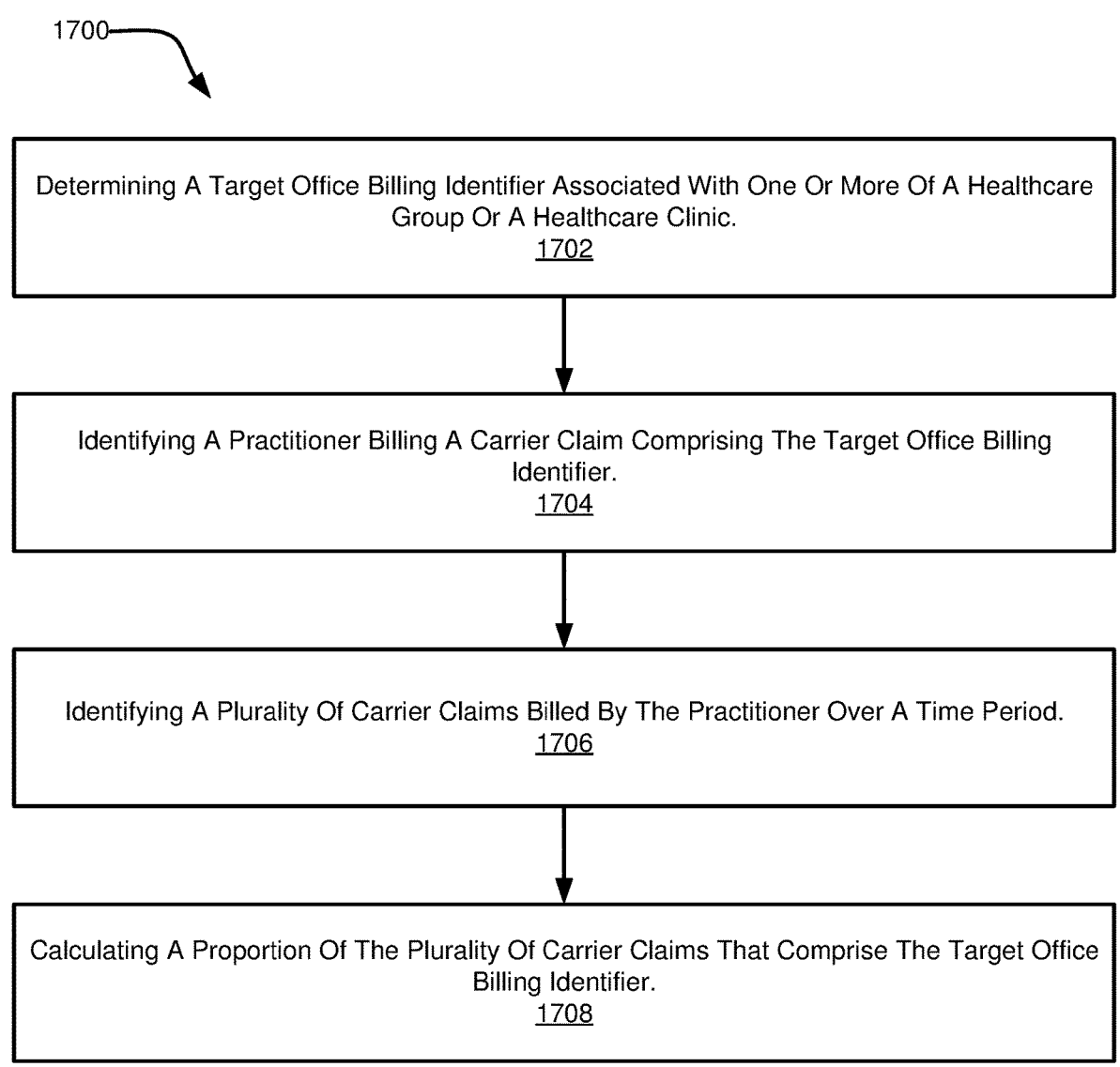
FIG. 17 is a schematic flow chart diagram of a method for assessing cohesion of a healthcare group's and/or healthcare clinic's billing practitioners.

FIG. 17 is a schematic flow chart diagram of a method 1700 for calculating cohesion metrics between healthcare entities. FIG. 17 may be particularly drawn to calculating billing capture 610 for carrier claims billed by practitioners 102 under a group 114. The billing capture 610 metric may apply to office billing 126 capture as identified based on carrier claims 402. The method 1700 may be performed by any suitable computing device and may be performed by one or more processors configurable to execute instructions stored in non-transitory computer readable storage media. The method 1700 may be performed by one or more computing devices that may be in communication with one another.

The method 1700 begins and a computing resource determines at 1702 a target office billing identifier associated with one or more of a healthcare group or a healthcare clinic. A computing resource identifies at 1704 a practitioner billing a carrier claim comprising the target office billing identifier. A computing resource identifies at 1706 a plurality of carrier claims billed by the practitioner over a time period. A computing resource calculates at 1708 a proportion of the plurality of carrier claims that comprise the target billing identifier.

Figure 18:
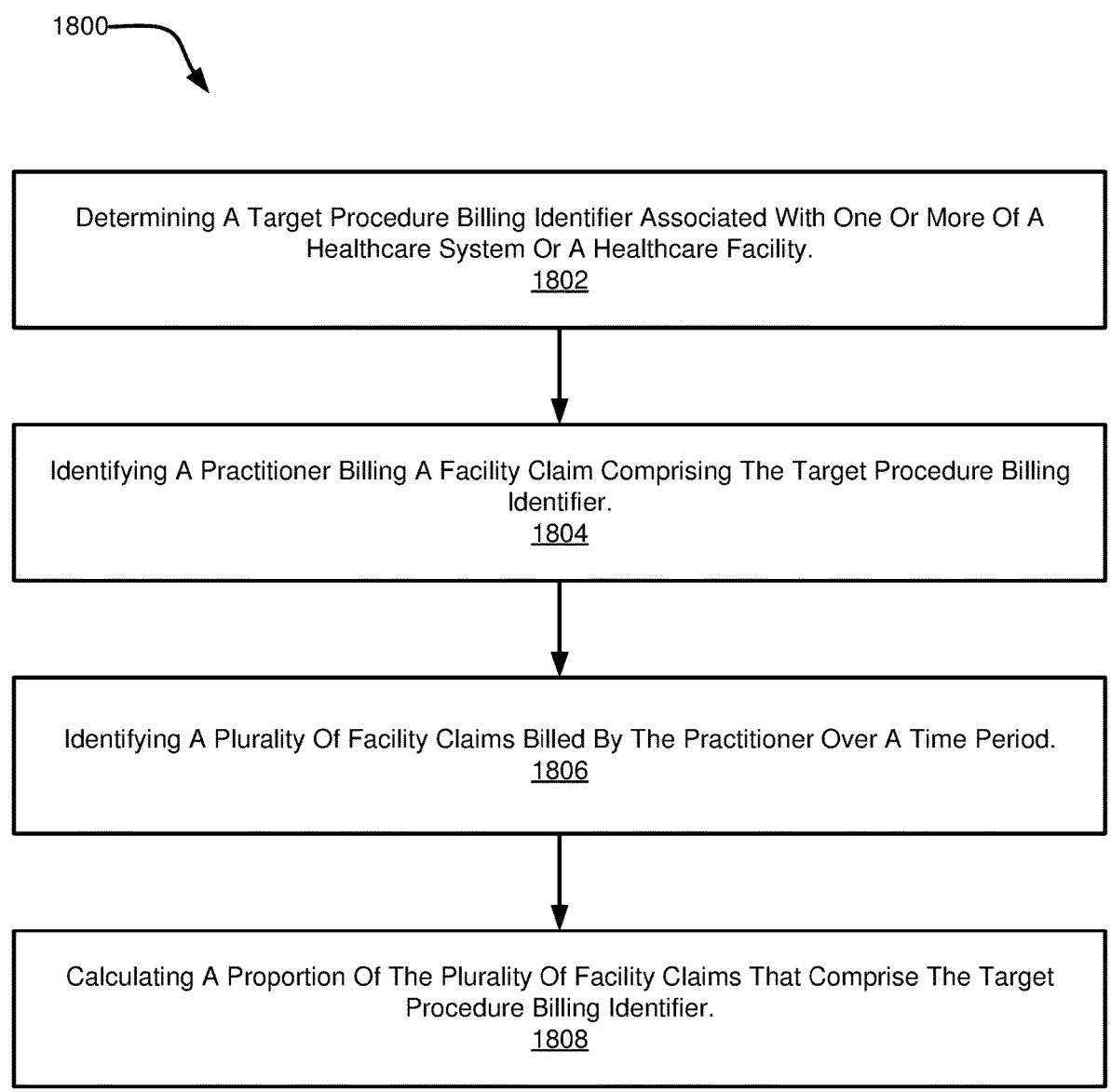
FIG. 18 is a schematic flow chart diagram of a method for assessing cohesion of a healthcare system's and/or healthcare facility's billing practitioners.

FIG. 18 is a schematic flow chart diagram of a method 1800 for calculating cohesion metrics between healthcare entities. FIG. 18 may be particularly drawn to calculating procedure capture 606 of services and procedures performed by a practitioner 102 at a facility 110 associated with a system 118. The procedure capture 606 metric may apply to procedure billing 122 as identified based on facility claims 404. The method 1800 may be performed by any suitable computing device and may be performed by one or more processors configurable to execute instructions stored in non-transitory computer readable storage media. The method 1800 may be performed by one or more computing devices that may be in communication with one another.

The method 1800 begins and a computing resource determines at 1802 a target procedure billing identifier associated with one or more of a healthcare system or a healthcare facility. A computing resource identifies at 1804 a practitioner billing a facility claim comprising the target procedure billing identifier. A computing resource identifies at 1806 a plurality of facility claims billed by the practitioner over a time period. A computing resource calculates at 1808 a proportion of the plurality of facility claims that comprise the target procedure billing identifier.

Figure 19:
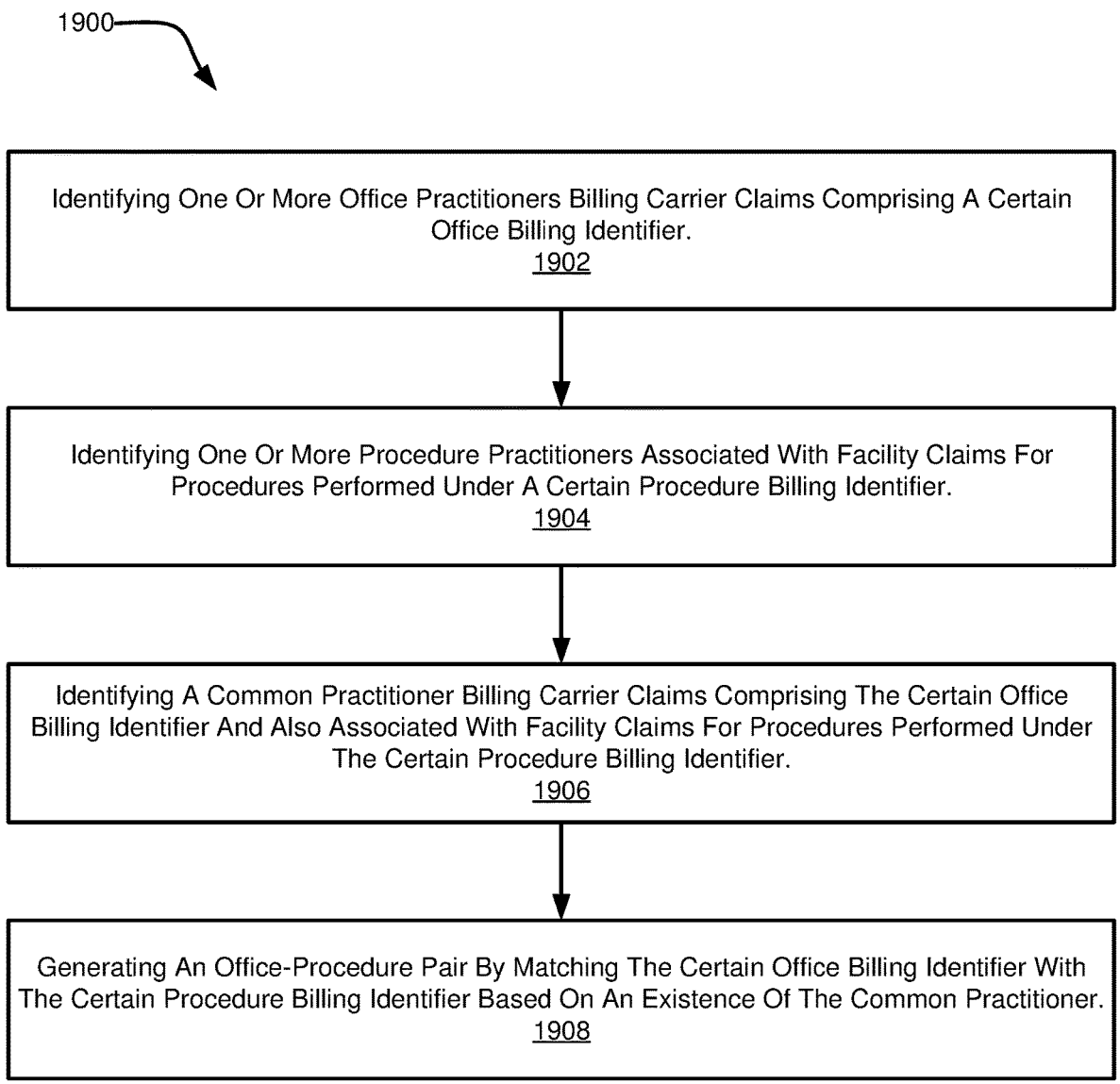
FIG. 19 is a schematic flow chart diagram of a method for assessing capture of a group's office and procedure claims performed by an associated system's practicing practitioners.

FIG. 19 is a schematic flow chart diagram of a method 1900 for calculating capture metrics between healthcare entities. The method 1900 may be performed by any suitable computing device and may be performed by one or more processors configurable to execute instructions stored in non-transitory computer readable storage media. The method 1900 may be performed by one or more computing devices that may be in communication with one another.

The method 1900 begins and a computing resource identifies at 1902 one or more office practitioners billing carrier claims comprising a certain office billing identifier. The certain office billing identifier may comprise one or more of a clinic identifier or a group identifier. The method 1900 continues and a computing resource identifies at 1904 one or more procedure practitioners associated with facility claims for procedures performed under a certain procedure billing identifier. The certain procedure billing identifier may be one or more of a facility identifier or a system identifier. The method 1900 continues and a computing resource identifies at 1906 a common practitioner billing carrier claims comprising the certain office billing identifier and also associated with facility claims for procedures performed under the certain procedure billing identifier. A computing resource generates at 1908 an office-procedure pair by matching the certain office billing identifier with the certain procedure billing identifier based on an existence of the common practitioner.

The method 1900 can be used to match healthcare groups 114 and healthcare systems 118 based on billed claims. In an embodiment, the office billing identifier 128 is a group identifier 116 and the procedure billing identifier 124 is a system identifier 120. In such an embodiment, the common practitioner represents a group-system practitioner that bills carrier claims under the group 114 and is further associated with facility claims for procedures performed at a facility 110 within the system 118. The existence of such a group-system practitioner can be used to link the group 114 and the system 118 for billing and other purposes. This information can be useful to certain entities who wish to understand real-world relationships between billing entities such as healthcare groups 114 and healthcare systems 118.

The method 1900 can further be used to match other healthcare entities within the group 114 and system 118 umbrellas. For example, a clinic 106 (within the group 114 umbrella) may be associated with a system 118 because a single practitioner is billing carrier claims under the clinic 106 and is additionally associated with facility claims for procedures performed at a facility 110 associated with the system 118. The method 1900 can be used to identify cross-relationships between systems 118 (and facilities 110 within the network of a certain system 118) and groups 114 (and clinics 106 within the network of a certain group 114).

The method 1900 can be used to identify any group-system relationship as discussed herein. The office-procedure pair generated at 1908 includes any group-system relationships discussed herein and may additionally include other relationships between procedure billing 122 entities and office billing 126 entities. These additional relationships may include associations between facilities 110, systems 118, clinics 106, and groups 114. The office-procedure pair may be used to calculate other metrics such as group-system employment 734, group-system procedure 738, group-system billing 740, group-system enrollment 742, and so forth. The office-procedure pair is a broader, generic term for a group-system pair. The office-procedure pair includes group-system pairs, clinic-facility pairs, clinic-system pairs, facility-group pairs, and so forth.

Figure 20:
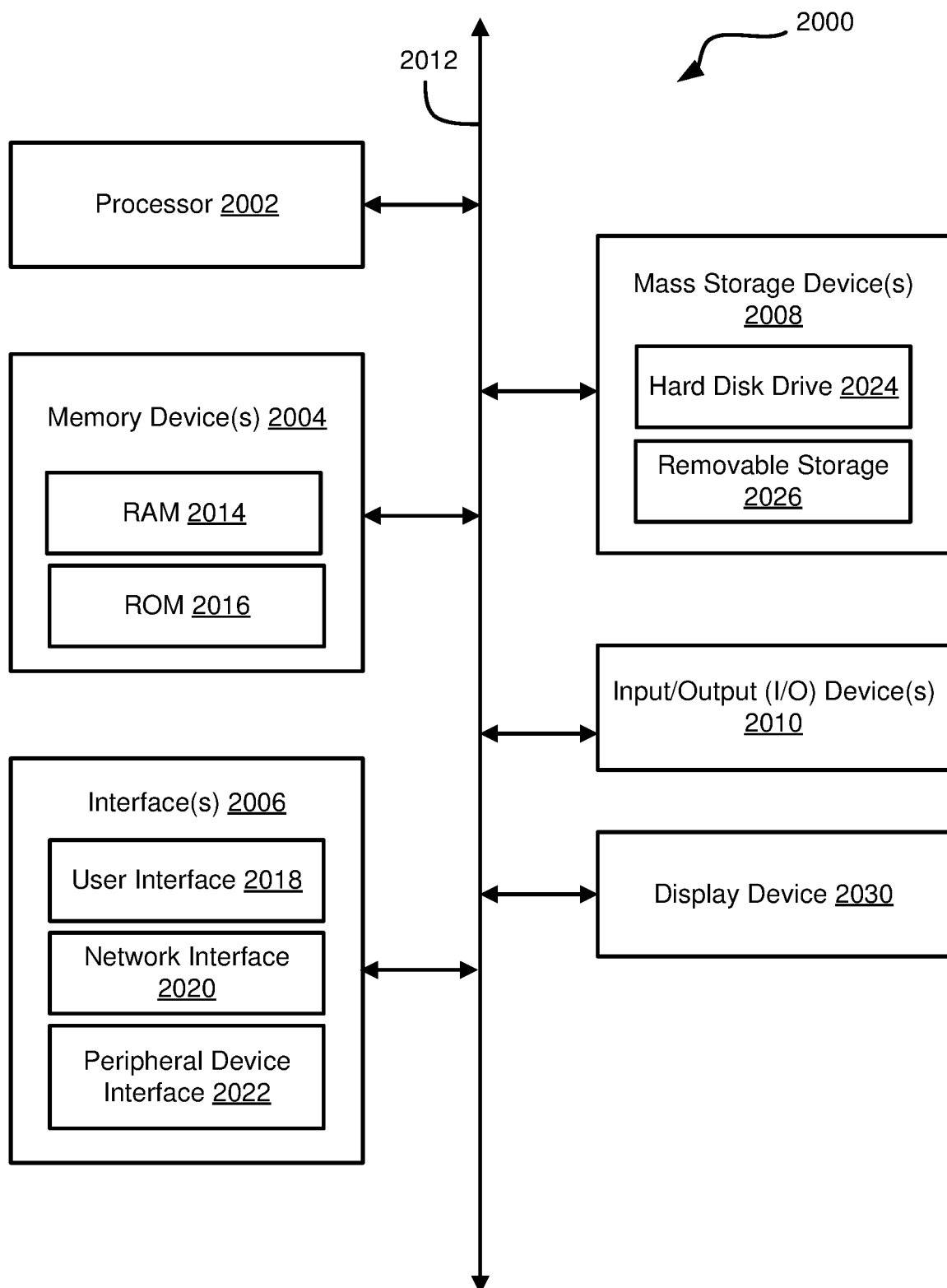
FIG. 20 is a schematic diagram illustrating components of an example computing device.

Referring now to FIG. 20, a block diagram of an example computing device 2000 is illustrated. Computing device 2000 may be used to perform various procedures, such as those discussed herein. Computing device 2000 can perform various monitoring functions as discussed herein, and can execute one or more application programs, such as the application programs or functionality described herein. Computing device 2000 can be any of a wide variety of computing devices, such as a desktop computer, in-dash computer, vehicle control system, a notebook computer, a server computer, a handheld computer, tablet computer and the like.

Computing device 2000 includes one or more processor(s) 2002, one or more memory device(s) 2004, one or more interface(s) 2006, one or more mass storage device(s) 2008, one or more Input/output (I/O) device(s) 2010, and a display device 2030 all of which are coupled to a bus 2012. Processor(s) 2002 include one or more processors or controllers that execute instructions stored in memory device(s) 2004 and/or mass storage device(s) 2008. Processor(s) 2002 may also include various types of computer-readable media, such as cache memory.

Memory device(s) 2004 include various computer-readable media, such as volatile memory (e.g., random access memory (RAM) 2014) and/or nonvolatile memory (e.g., read-only memory (ROM) 2016). Memory device(s) 2004 may also include rewritable ROM, such as Flash memory.

Mass storage device(s) 2008 include various computer readable media, such as magnetic tapes, magnetic disks, optical disks, solid-state memory (e.g., Flash memory), and so forth. As shown in FIG. 20, a particular mass storage device 2008 is a hard disk drive 2024. Various drives may also be included in mass storage device(s) 2008 to enable reading from and/or writing to the various computer readable media. Mass storage device(s) 2008 include removable media 2026 and/or non-removable media.

I/O device(s) 2010 include various devices that allow data and/or other information to be input to or retrieved from computing device 2000. Example I/O device(s) 2010 include cursor control devices, keyboards, keypads, microphones, monitors or other display devices, speakers, printers, network interface cards, modems, and the like.

Display device 2030 includes any type of device capable of displaying information to one or more users of computing device 2000. Examples of display device 2030 include a monitor, display terminal, video projection device, and the like.

Interface(s) 2006 include various interfaces that allow computing device 2000 to interact with other systems, devices, or computing environments. Example interface(s) 2006 may include any number of different network interfaces 2020, such as interfaces to local area networks (LANs), wide area networks (WANs), wireless networks, and the Internet. Other interface(s) include user interface 2018 and peripheral device interface 2022. The interface(s) 2006 may also include one or more user interface elements 2018. The interface(s) 2006 may also include one or more peripheral interfaces such as interfaces for printers, pointing devices (mice, track pad, or any suitable user interface now known to those of ordinary skill in the field, or later discovered), keyboards, and the like.

Bus 2012 allows processor(s) 2002, memory device(s) 2004, interface(s) 2006, mass storage device(s) 2008, and I/O device(s) 2010 to communicate with one another, as well as other devices or components coupled to bus 2012. Bus 2012 represents one or more of several types of bus structures, such as a system bus, PCI bus, IEEE bus, USB bus, and so forth.

EXAMPLES

The following examples pertain to further embodiments.

Example 1 is a method. The method includes determining a target office billing identifier associated with one or more of a healthcare group or a healthcare clinic. The method includes identifying a practitioner billing a carrier claim comprising the target office billing identifier. The method includes identifying a plurality of carrier claims billed by the practitioner over a time period. The method includes calculating a proportion of the plurality of carrier claims that comprise the target office billing identifier.

Example 2 is a method as in Example 1, further comprising: identifying one or more unique office billing identifiers associated with one or more additional healthcare groups and/or one or more additional healthcare clinics across the plurality of carrier claims billed by the practitioner; and for each of the one or more unique office billing identifiers, identifying one or more practitioners billing carrier claims comprising the one or more unique office billing identifiers.

Example 3 is a method as in any of Examples 1-2, wherein the target office billing identifier is associated with a certain healthcare group, and wherein the method further comprises calculating a clinic-practitioner billing cohesion metric by calculating a proportion of the plurality of carrier claims billed by the practitioner that were billed at a certain healthcare clinic associated with the certain healthcare group.

Example 4 is a method as in any of Examples 1-3, further comprising calculating clinic billing cohesion between the practitioner and the certain healthcare group by calculating sum of a squared clinic-practitioner billing cohesion metric.

Example 5 is a method as in any of Examples 1-4, further comprising: identifying one or more unique office billing identifiers across the plurality of carrier claims billed by the practitioner, wherein each of the one or more unique office billing identifiers is associated with a corresponding healthcare group; pairing the practitioner with each of the one or more unique office billing identifiers to generate one or more practitioner-group pairs; and for each of the one or more practitioner-group pairs, calculating a clinic-practitioner billing cohesion metric by calculating a proportion of the plurality of carrier claims that were performed at a clinic associated with the corresponding healthcare group.

Example 6 is a method as in any of Examples 1-5, further comprising, for each of the one or more practitioner-group pairs, calculating a group-practitioner procedure cohesion metric by calculating a proportion of the plurality of carrier claims billed by the practitioner that were performed at any clinic associated with the corresponding healthcare system.

Example 7 is a method as in any of Examples 1-6, further comprising, for each of the one or more practitioner-group pairs, calculating one or more of: a clinic procedure cohesion metric by calculating a sum of a squared clinic-practitioner procedure cohesion metric; or a group procedure cohesion metric by calculating a sum of a squared group-practitioner procedure cohesion metric.

Example 8 is a method as in any of Examples 1-7, further comprising: retrieving the plurality of carrier claims billed by the practitioner from a database; and executing an electronic data security measure with the database, wherein the electronic data security measure comprises one or more of securely communicating with a virtual datacenter associated with the database or de-encrypting encrypted data received from the database.

Example 9 is a method as in any of Examples 1-8, further comprising matching the carrier claim to a clinic to generate a matched claim, wherein matching the carrier claim to the clinic comprises matching based on: in a first matching iteration, a patient identifier for a patient that received a procedure from the practitioner, a date of service for the procedure performed, and a procedure code for the procedure; in a second matching iteration, the patient identifier, the date of service, and a practitioner ID associated with the practitioner; in a third matching iteration, an inpatient facility associated with the carrier claim if the carrier claim occurred during a hospitalization at the inpatient facility; in a fourth matching iteration, the date of service and a most common facility associated with the practitioner; and in a fifth matching iteration, the most common facility associated with the practitioner as determined based on a clinic ID in the carrier claim.

Example 10 is a method as in any of Examples 1-9, wherein matching the carrier claim to the clinic comprises matching based on: in a sixth matching iteration, the date of service and the most common facility associated with the practitioner; in a seventh matching iteration, the date of service and a recent most common facility associated with the practitioner based on carrier claims processed by the practitioner in a recent time period; in an eighth matching iteration, the date of service and the most common facility associated with the practitioner; in a ninth matching iteration, a most common facility associated with the practitioner using previously joined facilities; and in a tenth matching iteration, a facility most closely link to the clinic ID based on the carrier claim.

Example 11 is a method. The method includes determining a target procedure billing identifier associated with one or more of a healthcare system or a healthcare facility. The method includes identifying a practitioner billing a facility claim comprising the target procedure billing identifier. The method includes identifying a plurality of facility claims billed by the practitioner over a time period. The method includes calculating a proportion of the plurality of facility claims that comprise the target procedure billing identifier.

Example 12 is a method as in Example 11, further comprising: identifying one or more unique procedure billing identifiers associated with one or more additional healthcare systems and/or one or more additional healthcare facilities across the plurality of facility claims billed by the practitioner; and for each of the one or more unique procedure billing identifiers, identifying one or more practitioners billing facility claims comprising the one or more unique procedure billing identifiers.

Example 13 is a method as in any of Examples 11-12, wherein the target procedure billing identifier is associated with a certain healthcare system, and wherein the method further comprises calculating a facility-practitioner procedure cohesion metric by calculating a proportion of the plurality of facility claims billed by the practitioner that were billed at a certain healthcare facility associated with the certain healthcare system.

Example 14 is a method as in any of Examples 11-13, further comprising calculating facility procedure cohesion between the practitioner and the certain healthcare system by calculating a sum of a squared facility-practitioner procedure cohesion metric.

Example 15 is a method as in any of Examples 11-14, further comprising: identifying one or more unique procedure billing identifiers across the plurality of facility claims billed by the practitioner, wherein each of the one or more unique procedure billing identifiers is associated with a corresponding healthcare system; pairing the practitioner with each of the one or more unique procedure billing identifiers to generate one or more practitioner-system pairs; and for each of the one or more practitioner-system pairs, calculating a system-practitioner procedure cohesion metric by calculating a proportion of the plurality of facility claims that were performed at a facility associated with the corresponding healthcare system.

Example 16 is a method as in any of Examples 11-15, further comprising, for each of the one or more practitioner-system pairs, calculating a system-practitioner procedure cohesion metric by calculating a proportion of the plurality of facility claims billed by the practitioner that were performed at any facility associated with the corresponding healthcare system.

Example 17 is a method as in any of Examples 11-16, further comprising, for each of the one or more practitioner-system pairs, calculating one or more of: a facility procedure cohesion metric by calculating a sum of a squared facility-practitioner procedure cohesion metric; or a system procedure cohesion metric by calculating a sum of a squared system-practitioner procedure cohesion metric.

Example 18 is a method as in any of Examples 11-17, further comprising: retrieving the plurality of facility claims billed by the practitioner from a database; and executing an electronic data security measure with the database, wherein the electronic data security measure comprises one or more of securely communicating with a virtual datacenter associated with the database or de-encrypting encrypted data received from the database.

Example 19 is a method as in any of Examples 11-18, further comprising matching the carrier claim to a clinic to generate a matched claim, wherein matching the carrier claim to the clinic comprises matching based on: in a first matching iteration, a patient identifier for a patient that received a procedure from the practitioner, a date of service for the procedure performed, and a procedure code for the procedure; in a second matching iteration, the patient identifier, the date of service, and a practitioner ID associated with the practitioner; in a third matching iteration, an inpatient facility associated with the carrier claim if the carrier claim occurred during a hospitalization at the inpatient facility; in a fourth matching iteration, the date of service and a most common facility associated with the practitioner; and in a fifth matching iteration, the most common facility associated with the practitioner as determined based on a clinic ID in the carrier claim.

Example 20 is a method as in any of Examples 11-19, wherein matching the carrier claim to the clinic comprises matching based on: in a sixth matching iteration, the date of service and the most common facility associated with the practitioner; in a seventh matching iteration, the date of service and a recent most common facility associated with the practitioner based on carrier claims processed by the practitioner in a recent time period; in an eighth matching iteration, the date of service and the most common facility associated with the practitioner; in a ninth matching iteration, a most common facility associated with the practitioner using previously joined facilities; and in a tenth matching iteration, a facility most closely link to the clinic ID based on the carrier claim.

Example 21 is a method. the method includes identifying one or more office practitioners billing carrier claims comprising a certain office billing identifier. The method includes identifying one or more procedure practitioners associated with facility claims for procedures performed under a certain procedure billing identifier. The method includes identifying a common practitioner billing carrier claims comprising the certain office billing identifier and associated with facility claims for procedures performed under the certain procedure billing identifier. The method includes generating an office-procedure pair by matching the certain office billing identifier with the certain procedure billing identifier based on an existence of the common practitioner.

Example 22 is a method as in Example 21, further comprising calculating a proportion of procedures performed under the certain procedure billing identifier that were performed by the one or more office practitioners billing carrier claims comprising the certain office billing identifier.

Example 23 is a method as in any of Examples 21-22, further comprising calculating a proportion of carrier claims billed under the certain office billing identifier that were performed by the one or more procedure practitioners associated with facility claims for procedures performed under the certain procedure billing identifier.

Example 24 is a method as in any of Examples 21-23, wherein the certain procedure billing identifier is a system identifier associated with a healthcare system, and wherein the method further comprises: calculating a system billing affiliation metric for the common practitioner based on: total facility claims associated with the common practitioner performed at any of a plurality of healthcare systems over a time period; and total facility claims associated with the common practitioner performed at the healthcare system over the time period; and calculating a weighted procedure metric for the common practitioner by weighting a number of procedures performed by the common practitioner at the healthcare system.

Example 25 is a method as in any of Examples 21-24, further comprising: determining an individual National Provider Identifier (NPI) for each of the one or more office practitioners; and determining an individual NPI for each of the one or more procedure practitioners; wherein identifying the common practitioner comprises identifying a unique individual NPI listed on carrier claims billed under the certain office billing identifier and also listed on facility claims for procedures performed under the certain procedure billing identifier.

Example 26 is a method as in any of Examples 21-25, wherein identifying the common practitioner comprises determining there is the unique individual NPI listed on one or more carrier claims comprising the certain office billing identifier and also listed on one or more facility claims for procedures performed under the certain procedure billing identifier.

Example 27 is a method as in any of Examples 21-26, further comprising: calculating a capture by the certain office billing identifier of procedures performed under the certain procedure billing identifier based on a sum of squared shares of procedures performed under the certain procedure billing identifier by the one or more office practitioners; or calculating a capture by the certain procedure billing identifier for claims billed under the certain office billing identifier based on a sum of squared shares of carrier claims billed under the certain office billing identifier by the one or more procedure practitioners.

Example 28 is a method as in any of Examples 21-27, wherein the certain procedure billing identifier is a facility identifier associated with a healthcare facility, and wherein the method further comprises: calculating a facility billing affiliation metric for the common practitioner based on: total facility claims associated with the common practitioner performed at any of a plurality of healthcare facilities over a time period; and total facility claims associated with the common practitioner performed at the healthcare facility over the time period; and calculating a weighted procedure metric for the common practitioner by weighting a number of procedures performed by the common practitioner at the healthcare facility.

Example 29 is a method as in any of Examples 21-28, wherein the certain office billing identifier is a clinic identifier associated with a healthcare clinic, and wherein the method further comprises: calculating a clinic billing affiliation metric for the common practitioner based on: total carrier claims billed by the common practitioner over a time period; and total carrier claims billed by the common practitioner comprising the clinic identifier over the time period; and calculating a weighted office metric for the common practitioner by weighting a number of carrier claims billed by the common practitioner at the healthcare clinic.

Example 30 is a method as in any of Examples 21-29, further comprising: retrieving one or more of the carrier claims or the facility claims from a database; and executing an electronic data security measure with the database, wherein the electronic data security measure comprises one or more of securely communicating with a virtual datacenter associated with the database or de-encrypting encrypted data received from the database.

Example 31 is a system comprising one or more processors for executing instructions stored in non-transitory computer readable storage media, wherein the instructions comprise any of the method steps in Examples 1-30.

Example 32 is non-transitory computer readable storage media storing instructions for execution by one or more processors, wherein the instructions comprise any of the method steps in Examples 1-30.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium, which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, televisions, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. The terms "modules" and "components" are used in the names of certain components to reflect their implementation independence in software, hardware, circuitry, sensors, or the like. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein purposes of illustration and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A method comprising:
   securely communicating with a virtual data center provided by a healthcare entity, wherein the virtual data center comprises data security rules ensuring that raw carrier claims data downloaded from the virtual data center is downloaded in an encrypted format;
   aggregating data from a plurality of different data sources that comprises the virtual data center, wherein the data comprises the raw carrier claims data, and wherein the raw carrier claims data is ingested from the virtual data center in the encrypted format, and wherein the raw carrier claims data comprises all claims processed by a practitioner in a calendar year;

translating the raw carrier claims data by de-encrypting the raw carrier claims data from the encrypted format to a de-encrypted format, wherein the raw carrier claims data must be de-encrypted prior to analysis to calculate cohesion between the practitioner and one or more of a healthcare group or a healthcare clinic over the calendar year;

cleaning the de-encrypted raw carrier claims data by removing at least a portion of the de-encrypted raw carrier claims data to generate cleaned data, wherein the cleaned data comprises only information columns applicable to calculating the cohesion between the practitioner and the one or more of the healthcare group or the healthcare clinic over the calendar year;

generating a modeled version of the cleaned data by generating an intermediary file to reduce an amount of disc storage and Random Access Memory (RAM) required to assess the cleaned data to calculate the cohesion between the practitioner and the one or more of the healthcare group or the healthcare clinic over the calendar year, and wherein generating the intermediary file comprises partitioning the cleaned data based on one or more data metrics included in the cleaned data, wherein the one or more data metrics comprises calendar year and practitioner identifier;

linking the modeled version of the cleaned data to a database platform, wherein the database platform is built on modeled data sources rather than raw data sources, and wherein the database platform is in communication with a user interface that enables viewing of the cleaned data in the intermediary file;

querying the intermediary file on the database platform to identify a target office billing identifier associated with one or more of the healthcare group or the healthcare clinic;

querying the intermediary file on the database platform to identify at least one carrier claim stored within the intermediary file that comprises the target office billing identifier;

querying the intermediary file on the database platform to identify the practitioner associated with the at least one carrier claim that comprises the target office billing identifier;

querying the intermediary file on the database platform to identify a plurality of carrier claims stored within the intermediary file that were billed by the practitioner over the time period; and calculating a proportion of the plurality of carrier claims that comprise the target office billing identifier to determine cohesion between the practitioner and the one or more of the healthcare group or the healthcare clinic;

wherein the cohesion represents real-world relationships between the practitioner and the one or more of the healthcare group or the healthcare clinic that are given in near real-time based on the raw carrier claims data.

2. The method of claim 1, further comprising:

identifying one or more unique office billing identifiers associated with one or more additional healthcare groups and/or one or more additional healthcare clinics across the plurality of carrier claims billed by the practitioner; and for each of the one or more unique office billing identifiers, identifying one or more practitioners billing carrier claims comprising the one or more unique office billing identifiers.

3. The method of claim 1, wherein the target office billing identifier is associated with a certain healthcare group, and wherein the method further comprises calculating a clinic-practitioner billing cohesion metric by calculating a proportion of the plurality of carrier claims billed by the practitioner that were billed at a certain healthcare clinic associated with the certain healthcare group.

4. The method of claim 3, further comprising calculating clinic billing cohesion between the practitioner and the certain healthcare group by calculating sum of a squared clinic-practitioner billing cohesion metric.

5. The method of claim 1, further comprising:

identifying one or more unique office billing identifiers across the plurality of carrier claims billed by the practitioner, wherein each of the one or more unique office billing identifiers is associated with a corresponding healthcare group;

pairing the practitioner with each of the one or more unique office billing identifiers to generate one or more practitioner-group pairs; and for each of the one or more practitioner-group pairs, calculating a clinic-practitioner billing cohesion metric by calculating a proportion of the plurality of carrier claims that were performed at a clinic associated with the corresponding healthcare group.

6. The method of claim 5, further comprising, for each of the one or more practitioner-group pairs, calculating a group-practitioner billing cohesion metric by calculating a proportion of the plurality of carrier claims billed by the practitioner that were performed at any clinic associated with the corresponding healthcare group.

7. The method of claim 5, further comprising, for each of the one or more practitioner-group pairs, calculating one or more of:

a clinic billing cohesion metric by calculating a sum of a squared clinic-practitioner billing cohesion metric; or a group billing cohesion metric by calculating a sum of a squared group-practitioner billing cohesion metric.

8. The method of claim 1, wherein aggregating the data from the plurality of different data sources comprises retrieving the raw carrier claims from a database; and wherein the method further comprises executing an electronic data security measure with the database comprising one or more of securely communicating with a virtual datacenter associated with the database or de-encrypting encrypted data received from the database.

9. The method of claim 1, further comprising matching the at least one carrier claim to a facility to generate a matched claim, wherein matching the at least one carrier claim to the facility comprises matching based on:

in a first matching iteration, a patient identifier for a patient that received a procedure from the practitioner, a date of service for the procedure performed, and a procedure code for the procedure;

in a second matching iteration, the patient identifier, the date of service, and a practitioner ID associated with the practitioner;

in a third matching iteration, an inpatient facility associated with the carrier claim if the carrier claim occurred during a hospitalization at the inpatient facility;

in a fourth matching iteration, the date of service and a most common facility associated with the practitioner; and in a fifth matching iteration, the most common facility associated with the practitioner as determined based on a clinic ID in the carrier claim.

10. The method of claim 9, wherein matching the at least one carrier claim to the facility comprises matching based on:
   in a sixth matching iteration, the date of service and the most common facility associated with the practitioner;
   in a seventh matching iteration, the date of service and a recent most common facility associated with the practitioner based on carrier claims processed by the practitioner in a recent time period;
   in an eighth matching iteration, the date of service and the most common facility associated with the practitioner;
   in a ninth matching iteration, a most common facility associated with the practitioner using previously joined facilities; and
   in a tenth matching iteration, a facility most closely link to the clinic ID based on the carrier claim.

11. A system comprising one or more processors for executing instructions stored in non-transitory computer readable storage media, the instructions comprising:
   securely communicating with a virtual data center provided by a healthcare entity, wherein the virtual data center comprises data security rules ensuring that raw carrier claims data downloaded from the virtual data center is downloaded in an encrypted format;
   aggregating data from a plurality of different data sources that comprises the virtual data center, wherein the data comprises the raw carrier claims data, and wherein the raw carrier claims data is ingested from the virtual data center in the encrypted format, and wherein the raw carrier claims data comprises all claims processed by a practitioner in a calendar year;
   translating the raw carrier claims data by de-encrypting the raw carrier claims data from the encrypted format to a de-encrypted format, wherein the raw carrier claims data must be de-encrypted prior to analysis to calculate cohesion between the practitioner and one or more of a healthcare group or a healthcare clinic over the calendar year;
   cleaning the de-encrypted raw carrier claims data by removing at least a portion of the de-encrypted raw carrier claims data to generate cleaned data, wherein the cleaned data comprises only information columns applicable to calculating the cohesion between the practitioner and the one or more of the healthcare group or the healthcare clinic over the calendar year;
   generating a modeled version of the cleaned data by generating an intermediary file to reduce an amount of disc storage and Random Access Memory (RAM) required to assess the cleaned data to calculate the cohesion between the practitioner and the one or more of the healthcare group or the healthcare clinic over the calendar year, and wherein generating the intermediary file comprises partitioning the cleaned data based on one or more data metrics included in the cleaned data, wherein the one or more data metrics comprises calendar year and practitioner identifier;
   linking the modeled version of the cleaned data to a database platform, wherein the database platform is built on modeled data sources rather than raw data sources, and wherein the database platform is in communication with a user interface that enables viewing of the cleaned data in the intermediary file;
   querying the intermediary file on the database platform to identify a target office billing identifier associated with one or more of the healthcare group or the healthcare clinic;
   querying the intermediary file on the database platform to identify at least one carrier claim stored within the intermediary file that comprises the target office billing identifier;
   querying the intermediary file on the database platform to identify the practitioner associated with the at least one carrier claim that comprises the target office billing identifier;
   querying the intermediary file on the database platform to identify a plurality of carrier claims stored within the intermediary file that were billed by the practitioner over the time period; and
   calculating a proportion of the plurality of carrier claims that comprise the target office billing identifier to determine cohesion between the practitioner and the one or more of the healthcare group or the healthcare clinic;
   wherein the cohesion represents real-world relationships between the practitioner and the one or more of the healthcare group or the healthcare clinic that are given in near real-time based on the raw carrier claims data.

12. The system of claim 11, wherein the instructions further comprise:
   identifying one or more unique office billing identifiers associated with one or more additional healthcare groups and/or one or more additional healthcare clinics across the plurality of carrier claims billed by the practitioner; and
   for each of the one or more unique office billing identifiers, identifying one or more practitioners billing carrier claims comprising the one or more unique office billing identifiers.

13. The system of claim 11, wherein the target office billing identifier is associated with a certain healthcare group, and wherein the instructions further comprise calculating a clinic-practitioner billing cohesion metric by calculating a proportion of the plurality of carrier claims billed by the practitioner that were billed at a certain healthcare clinic associated with the certain healthcare group.

14. The system of claim 13, wherein the instructions further comprise calculating clinic billing cohesion between the practitioner and the certain healthcare group by calculating sum of a squared clinic-practitioner billing cohesion metric.

15. The system of claim 11, wherein the instructions further comprise:
   identifying one or more unique office billing identifiers across the plurality of carrier claims billed by the practitioner, wherein each of the one or more unique office billing identifiers is associated with a corresponding healthcare group;
   pairing the practitioner with each of the one or more unique office billing identifiers to generate one or more practitioner-group pairs; and
   for each of the one or more practitioner-group pairs, calculating a clinic-practitioner billing cohesion metric by calculating a proportion of the plurality of carrier claims that were performed at a clinic associated with the corresponding healthcare group.

16. The system of claim 15, wherein the instructions further comprise, for each of the one or more practitioner-group pairs, calculating a group-practitioner billing cohesion metric by calculating a proportion of the plurality of carrier claims billed by the practitioner that were performed at any clinic associated with the corresponding healthcare group.

17. The system of claim 15, wherein the instructions further comprise, for each of the one or more practitioner-group pairs, calculating one or more of:
   a clinic billing cohesion metric by calculating a sum of a squared clinic-practitioner billing cohesion metric; or
   a group billing cohesion metric by calculating a sum of a squared group-practitioner billing cohesion metric.

18. The system of claim 11, wherein the instructions are such that aggregating the data from the plurality of different data sources comprises retrieving the raw carrier claims from a database; and
   wherein the instructions further comprise executing an electronic data security measure with the database comprising one or more of securely communicating with a virtual datacenter associated with the database or de-encrypting encrypted data received from the database.

19. The system of claim 11, wherein the instructions further comprise matching the at least one carrier claim to a facility to generate a matched claim, wherein matching the at least one carrier claim to the facility comprises matching based on:
   in a first matching iteration, a patient identifier for a patient that received a procedure from the practitioner, a date of service for the procedure performed, and a procedure code for the procedure;
   in a second matching iteration, the patient identifier, the date of service, and a practitioner ID associated with the practitioner;
   in a third matching iteration, an inpatient facility associated with the carrier claim if the carrier claim occurred during a hospitalization at the inpatient facility;
   in a fourth matching iteration, the date of service and a most common facility associated with the practitioner; and
   in a fifth matching iteration, the most common facility associated with the practitioner as determined based on a clinic ID in the carrier claim.

20. The system of claim 19, wherein the instructions are such that matching the at least one carrier claim to the facility comprises matching based on:
   in a sixth matching iteration, the date of service and the most common facility associated with the practitioner;
   in a seventh matching iteration, the date of service and a recent most common facility associated with the practitioner based on carrier claims processed by the practitioner in a recent time period;
   in an eighth matching iteration, the date of service and the most common facility associated with the practitioner;
   in a ninth matching iteration, a most common facility associated with the practitioner using previously joined facilities; and
   in a tenth matching iteration, a facility most closely linked to the clinic ID based on the carrier claim.

21. Non-transitory computer readable storage media storing instructions for execution by one or more processors, the instructions comprising:
   securely communicating with a virtual data center provided by a healthcare entity, wherein the virtual data center comprises data security rules ensuring that raw carrier claims data downloaded from the virtual data center is downloaded in an encrypted format;
   aggregating data from a plurality of different data sources that comprises the virtual data center, wherein the data comprises the raw carrier claims data, and wherein the raw carrier claims data is ingested from the virtual data center in the encrypted format, and wherein the raw carrier claims data comprises all claims processed by a practitioner in a calendar year;
   translating the raw carrier claims data by de-encrypting the raw carrier claims data from the encrypted format to a de-encrypted format, wherein the raw carrier claims data must be de-encrypted prior to analysis to calculate cohesion between the practitioner and one or more of a healthcare group or a healthcare clinic over the calendar year;
   cleaning the de-encrypted raw carrier claims data by removing at least a portion of the de-encrypted raw carrier claims data to generate cleaned data, wherein the cleaned data comprises only information columns applicable to calculating the cohesion between the practitioner and the one or more of the healthcare group or the healthcare clinic over the calendar year;
   generating a modeled version of the cleaned data by generating an intermediary file to reduce an amount of disc storage and Random Access Memory (RAM) required to assess the cleaned data to calculate the cohesion between the practitioner and the one or more of the healthcare group or the healthcare clinic over the calendar year, and wherein generating the intermediary file comprises partitioning the cleaned data database platform based on one or more data metrics included in the cleaned data, wherein the one or more data metrics comprises calendar year and practitioner identifier;
   linking the modeled version of the cleaned data to a database platform, wherein the database platform is built on modeled data sources rather than raw data sources, and wherein the database platform is in communication with a user interface that enables viewing of the cleaned data in the intermediary file;
   querying the intermediary file on the database platform to identify a target office billing identifier associated with one or more of the healthcare group or the healthcare clinic;
   querying the intermediary file on the database platform to identify at least one carrier claim stored within the intermediary file that comprises the target office billing identifier;
   querying the intermediary file on the database platform to identify the practitioner associated with the at least one carrier claim that comprises the target office billing identifier;
   querying the intermediary file on the database platform to identify a plurality of carrier claims stored within the intermediary file that were billed by the practitioner over the time period; and
   calculating a proportion of the plurality of carrier claims that comprise the target office billing identifier to determine cohesion between the practitioner and the one or more of the healthcare group or the healthcare clinic;
   wherein the cohesion represents real-world relationships between the practitioner and the one or more of the healthcare group or the healthcare clinic that are given in near real-time based on the raw carrier claims data.

22. The non-transitory computer readable storage media of claim 21, wherein the instructions further comprise:
   identifying one or more unique office billing identifiers associated with one or more additional healthcare groups and/or one or more additional healthcare clinics across the plurality of carrier claims billed by the practitioner; and for each of the one or more unique office billing identifiers, identifying one or more practitioners billing carrier claims comprising the one or more unique office billing identifiers.

23. The non-transitory computer readable storage media of claim 21, wherein the target office billing identifier is associated with a certain healthcare group, and wherein the instructions further comprise calculating a clinic-practitioner billing cohesion metric by calculating a proportion of the plurality of carrier claims billed by the practitioner that were billed at a certain healthcare clinic associated with the certain healthcare group.

24. The non-transitory computer readable storage media of claim 23, wherein the instructions further comprise calculating clinic billing cohesion between the practitioner and the certain healthcare group by calculating sum of a squared clinic-practitioner billing cohesion metric.

25. The non-transitory computer readable storage media of claim 21, wherein the instructions further comprise:
   identifying one or more unique office billing identifiers across the plurality of carrier claims billed by the practitioner, wherein each of the one or more unique office billing identifiers is associated with a corresponding healthcare group;
   pairing the practitioner with each of the one or more unique office billing identifiers to generate one or more practitioner-group pairs; and
   for each of the one or more practitioner-group pairs, calculating a clinic-practitioner billing cohesion metric by calculating a proportion of the plurality of carrier claims that were performed at a clinic associated with the corresponding healthcare group.

26. The non-transitory computer readable storage media of claim 25, wherein the instructions further comprise, for each of the one or more practitioner-group pairs, calculating a group-practitioner billing cohesion metric by calculating a proportion of the plurality of carrier claims billed by the practitioner that were performed at any clinic associated with the corresponding healthcare group.

27. The non-transitory computer readable storage media of claim 25, wherein the instructions further comprise, for each of the one or more practitioner-group pairs, calculating one or more of:
   a clinic billing cohesion metric by calculating a sum of a squared clinic-practitioner billing cohesion metric; or
   a group billing cohesion metric by calculating a sum of a squared group-practitioner billing cohesion metric.

28. The non-transitory computer readable storage media of claim 21, wherein the instructions are such that aggregating the data from the plurality of different data sources comprises retrieving the raw carrier claims from a database; and
   wherein the instructions further comprise executing an electronic data security measure with the database comprising one or more of securely communicating with a virtual datacenter associated with the database or de-encrypting encrypted data received from the database.

29. The non-transitory computer readable storage media of claim 21, wherein the instructions further comprise matching the at least one carrier claim to a facility to generate a matched claim, wherein matching the at least one carrier claim to the facility comprises matching based on:
   in a first matching iteration, a patient identifier for a patient that received a procedure from the practitioner, a date of service for the procedure performed, and a procedure code for the procedure;
   in a second matching iteration, the patient identifier, the date of service, and a practitioner ID associated with the practitioner;
   in a third matching iteration, an inpatient facility associated with the carrier claim if the carrier claim occurred during a hospitalization at the inpatient facility;
   in a fourth matching iteration, the date of service and a most common facility associated with the practitioner; and
   in a fifth matching iteration, the most common facility associated with the practitioner as determined based on a clinic ID in the carrier claim.

30. The non-transitory computer readable storage media of claim 29, wherein the instructions are such that matching the at least one carrier claim to the facility comprises matching based on:
   in a sixth matching iteration, the date of service and the most common facility associated with the practitioner;
   in a seventh matching iteration, the date of service and a recent most common facility associated with the practitioner based on carrier claims processed by the practitioner in a recent time period;
   in an eighth matching iteration, the date of service and the most common facility associated with the practitioner;
   in a ninth matching iteration, a most common facility associated with the practitioner using previously joined facilities; and
   in a tenth matching iteration, a facility most closely link to the clinic ID based on the carrier claim.

\* \* \* \* \*